United States Patent
Chi et al.

(10) Patent No.: US 11,661,630 B2
(45) Date of Patent: May 30, 2023

(54) COMPOSITIONS AND METHODS FOR BLOOD STORAGE

(71) Applicant: Duke University, Durham, NC (US)

(72) Inventors: Jen-Tsan Ashley Chi, Durham, NC (US); Jennifer Doss, Durham, NC (US); Katelyn Walzer, Durham, NC (US)

(73) Assignee: Duke University

( * ) Notice: Subject to any disclaimer, the term of this patent is extended or adjusted under 35 U.S.C. 154(b) by 242 days.

(21) Appl. No.: 16/091,391

(22) PCT Filed: Apr. 6, 2017

(86) PCT No.: PCT/US2017/026390
§ 371 (c)(1),
(2) Date: Oct. 4, 2018

(87) PCT Pub. No.: WO2017/177028
PCT Pub. Date: Oct. 12, 2017

(65) Prior Publication Data
US 2019/0153536 A1    May 23, 2019

Related U.S. Application Data

(60) Provisional application No. 62/318,821, filed on Apr. 6, 2016.

(51) Int. Cl.
*C12Q 1/6876* (2018.01)
*G01N 33/80* (2006.01)
*G01N 33/96* (2006.01)
*G01N 33/94* (2006.01)

(52) U.S. Cl.
CPC .......... *C12Q 1/6876* (2013.01); *G01N 33/80* (2013.01); *G01N 33/94* (2013.01); *G01N 33/96* (2013.01); *C12Q 2600/158* (2013.01); *C12Q 2600/178* (2013.01)

(58) Field of Classification Search
CPC .......... C12Q 1/6876; C12Q 2600/158; C12Q 2600/178; G01N 33/80; G01N 33/94; G01N 33/96
See application file for complete search history.

(56) References Cited

U.S. PATENT DOCUMENTS

| | | |
|---|---|---|
| 2009/0326051 A1 | 12/2009 | Corey et al. |
| 2012/0244530 A1 | 9/2012 | Michot et al. |
| 2014/0235697 A1 | 8/2014 | Weiner et al. |
| 2016/0068914 A1 | 3/2016 | Newbury et al. |

OTHER PUBLICATIONS

Leuenberger et al. (PLoS One, 2013 vol. 8:pp. 1-9, plus Supplementary Tables).*

(Continued)

*Primary Examiner* — Terra C Gibbs
(74) *Attorney, Agent, or Firm* — Polsinelli PC

(57) ABSTRACT

The present disclosure relates to compositions and methods for determining the quality of stored blood and detecting Autologous Blood Transfusions (ABT) and blood doping.

20 Claims, 31 Drawing Sheets

Specification includes a Sequence Listing.

(56) References Cited

OTHER PUBLICATIONS

Qiagen miRNA easy kit includes miR-720, with the sequence of ucucgcuggggccucca as evidenced by Qiagen Version 13-Human-List-EN (1).pdf downloaded from https://www.qiagen.com/us/resources/download.aspx?id=a1c123d9-fdb8-4fc7-b18b-c9782baec931&lang=en on Dec. 22, 2020.*
JPAC, Autologous blood transfusion (collection and reinfusion of the patient's own red blood cells) (transfusionguidelines.org) downloaded on Dec. 6, 2021.*
Wen-Hsuan Yang (Dissertation, Duke University, Department of Biochemistry (2019)).*
Yang et al. (Br J Haemtaol., 2019 vol. 185:760-764).*
Sarachana et al. (Transfusion, 2015 vol. 55:2672-2683).*
Written Opinion and International Search Report for PCT/US2017/026390, dated Oct. 12, 2017.
D'Alessandro, A et al., An update on red blood cell storage lesions, as gleaned through biochemistry and omics technologies. Transfusion. Jan. 2015. vol. 55, pp. 205-219.
Dean, MM et al., Donor Variation In Biological Mediators During Storage of Packed Red Blood Cells. Blood. 2013. vol. 122, Issue 21, abstract.
Hao, et al., Bioinformatic analysis of microRNA expression in Parkinson's disease. Molecular Medicine Reports. 2015. vol. 11, pp. 1079-1084.
Kannan, et al., Differential profiling of human red blood cells during storage for 52 selected microRNAs, Jul. 2010. Transfusion, vol. 50, No. 7, Abstract.
Leuenberger, et al. Circulating microRNAs as Biomarkers for Detection of Autologous Blood Transfusion. PLoS One. Jun. 20, 2013. vol. 8, No. 6, e66309.
Long, et al., MiR-582-5p/miR-590-5p targeted CREB1/CREB5-NF-KB signaling and caused opioid-induced immunosuppression in human monocytes. Translational Psychiatry. Mar. 15, 2016, vol. 6, e757.
Mi, et al., miR-33a-5p modulates TNF-a-inhibited osteogenic differentiation by targeting SATB2 expression in nBMSCs. FEBS Letters. Feb. 3, 2016. vol. 590, pp. 396-407.
Pizzo, et al., Ribonuclease/angiogenin inhibitor 1 regulates stressinduced subcellular localization of angiogenin to control growth and survival. Journal of Cell Science. 2013. vol 126, pp. 4308-4319.
Pontes, et al., The miRNA Profile of Platelets Stored in a Blood Bank and Its Relation to Cellular Damage from Storage. PLoS One. Jun. 29, 2015. vol. 10, No. 6, e0129399.
Stenvang, et al., Inhibition of microRNA function by antimiR oligonucleotides. Silence. 2012. vol. 3, No. 1.
Accession No. MIMAT0000091, 2001.
Accession No. MIMAT0003227, 2006.
Accession No. MIMAT0003247, 2006.
Accession No. MIMAT0005954, 2011.
Balsara et al. (2008) "Plasminogen activator inhibitor-1: The double-edged sword in apoptosis," Thrombosis and Haemostasis 100:1029-36.
Bruchova et al. (2007) "Regulated expression of microRNAs in normal and polycythemia vera erythropoiesis," Experimental Hematology 35:1657-67.
Byon et al. (2014) "Deletion of Dicer in late erythroid cells results in impaired stress erythropoiesis in mice," Experimental Hematology.
Chang et al. (2006) "GATHER: a systems approach to interpreting genomic signatures," Bioinformatics 22:2926-33.
Chen et al. (2007) "Endofin, a FYVE Domain Protein, Interacts with Smad4 and Facilitates Transforming Growth Factor-B Signaling," The Journal of Biological Chemistry 282:9688-95.
Chen et al. (2008) "The Genomic Analysis of Lactic Acidosis and Acidosis Response in Human Cancers," PLoS Genet 4:e1000293.
Chen et al. (2008) "The Genomic Analysis of Erythrocyte microRNA Expression in Sickle Cell Diseases," PLoS One 3: e2360.
Chen et al. (2010) "Lactic Acidosis Triggers Starvation Response with Paradoxical Induction of TXNIP through MiondoA," PLoS Genet. 6.
Choi et al. (2005) "Tsc-22 enhances TGF-β signaling by associating with Smad4 and induces erythroid cell differentiation," Molecular and Cellular Biochemistry 271:23-8.
Conboy et al. (1986) "Molecular cloning of protein 4.1, a major structural element of the human erythrocyte membrane skeleton," Proc. Natl. Acad. Sci. USA 83:9512-6.
Dennler et al. (1998) "Direct binding of Smad3 and Smad4 to critical TGFβ-inducible elements in the promoter of human plasminogen activator inhibitor-type 1 gene," The EMBO Journal 17:3091-100.
Dong et al. (2014) "GATA-2 inhibits transforming growth factor-β signaling pathway through interaction with Smad4," Cellular Signaling 26:1089-97.
Dore et al. (2008) "A GATA-1-regulated microRNA locus essential for erythropoiesis," Proc. Natl. Acad. Sci. USA 105:3333-8.
Doss et al. (2015) "A comprehensive joint analysis of the long and short RNA transcriptomes of human erythrocytes," BMC Genomic 16:952.
Dussiot et al. (2014) "An activin receptor IIA ligand trap corrects ineffective erythropoiesis in β-thalassemia," Nature Medicine 20:398-407.
Emara et al. (2010) "Angiogenin-induced tRNA-derived Stress-induced RNAs Promote Stress-induced Stress Granule Assembly," J. Biol. Chem. 285:10959-68.
Ferrandiz et al. (2012) "p21 as a Transcriptional Co-Repressor of S-Phase and Mitotic Control Genes," PloS One 7: e37759.
Friedlander et al. (2008) "Discovering microRNAs from deep sequencing data using miRDeep," Nat Biotechnol. 26:407-15.
Friedlander et al. (2012) "miRDeep2 accurately identifies known and hundreds of novel microRNA genes in seven animal clades," Nucleic Acids Research 40:37-52.
Fu et al. (2009) "Mir-144 selectively regulates embryonic—hemoglobin synthesis during primitive erythropoiesis," Blood 113:1340-9.
Hara et al. (2013) "miRNA-720 Controls Stem Cell Phenotype, Proliferation and Differentiation of Human Dental Pulp Cells," PLoS One 8:e83545.
Harada et al. (2003) "Apoptosis Regulators," Reviews in Clinical and Experimental Hematology 7:117-38.
He et al. (2006) "Hematopoiesis Controlled by Distinct TIF1g and Smad4 Branches of the TGFb Pathway," Cell 125:929-41.
Ivanov et al. (2011) "Angiogenin-Induced tRNA Fragments Inhibit Translation Initiation," Mol. Cell. 43:613-23.
Jima et al. (2010) ",Deep sequencing of the small RNA transcriptome of normal and malignant human B cells identifies hundreds of novel microRNAs" Blood 116:e118-27.
Kilberg et al. (2009) "ATF4-dependent transcription mediates signaling of amino acid limitation," Trends Endocrinol Metab. 20:436-43.
Kirschner et al. (2011) "Haemolysis during Sample Preparation Alters microRNA Content of Plasma," PloS One 6: e24145.
Kohno et al. (2014) "Management of erythropoiesis: cross-sectional study of the relationships between erythropoiesis and nutrition, physical features, and adiponectin in 3519 Japanese people," European Journal of Haematology 92:298-307.
LaMonte et al. (2012) "Translocation of Sickle Cell Erythrocyte MicroRNAs into Plasmodium falciparum Inhibits Parasite Translation and Contributes to Malaria Resistance," Cell Host Microbe. 12:187-99.
Lewis et al. (2005) "Conserved Seed Pairing, Often Flanked by Adenosines, Indicates that Thousands of Human Genes are MicroRNA Targets," Cell 120:15-20.
Li et al. (2014) "miR-720 inhibits tumor invasion and migration in breast cancer by targeting TWIST1," Carcinogenesis 35:469-78.
McDonald et al. (2011) "Analysis of Circulating MicroRNA: Preanalytical and Analytical Challenges," Clin Chem. 57:833-40.
Nakao et al. (1997) "TGF-β receptor-mediated signalling through Smad2, Smad3 and Smad4," The EMBO Journal 16:5353-62.
Noh et al. (2009) "Let-7 microRNAs are developmentally regulated in circulating human erythroid cells," J. Transl. Med. 7:98.

(56) References Cited

OTHER PUBLICATIONS

Nonaka et al. (2015) "Circulating miR-103 and miR-720 as novel serum biomarkers for patients with colorectal cancer," Int. J. Oncol. 47:1097-102.
Patrick et al. (2010) "Defective erythroid differentiation in miR-451 mutant mice mediated by 14-3-3z," Genes Dev. 24:1614-9.
Pimentel et al. (2014) "A dynamic alternative splicing program regulates gene expression during terminal erythropoiesis," Nucleic Acids Research 42:4031-42.
Ponka, et al. (1998) "Function and Regulation of Transferrin and Ferritin," Seminars in Hematology, 35:35-54.
Pottgiesser et al. (2009) "Gene expression in the detection of autologous blood transfusion in sports—a pilot study," Vox sanguinis 96:333-6.
Pritchard et al. (2012) "Blood Cell Origin of Circulating MicroRNAs: A Cautionary Note for Cancer Biomarker Studies," Cancer Prevention Research 5:492-7.
Randrianarison-Huetz et al. (2010) "Gfi-1B controls human erythroid and megakaryocytic differentiation by regulating TGF-B signaling at the bipotent erythro-megakaryocytic progenitor stage," Blood 115:2784-95.
Rathjen et al. (2006) "Analysis of short RNAs in the malaria parasite and its red blood cell host," FEBS Lett. 580:5185-8.
Sangokoya et al. (2010) "microRNA miR-144 modulates oxidative stress tolerance and associates with anemia severity in sickle cell disease," Blood 116:4338-48.
Sangokoya et al. (2010) "Isolation and Characterization of MicroRNAs of Human Mature Erythrocytes," Methods of Molecular Biology 667:193-203.
Sarachana et al. (2015) "Evaluation of small noncoding RNAs in ex vivo stored human mature red blood cells: changes in noncoding RNA levels correlate with storage lesion events," Transfusion 55:2672-83.
Sharbati et al. (2010) "Deciphering the porcine intestinal microRNA transcriptome," BMC Genomics 11:275.
Shaw et al. (2006) "Mitoferrin is essential for erythroid iron assimilation," Nature 440:96-100.
Shinozuka et al. (2013) "SnoN/SKIL modulates proliferation through control of hsa-miR-720 transcription in esophageal cancer cells," Biochem Biophys Res. Commun. 430:101-6.
Suragani et al. (2014) "Transforming growth factor-β superfamily ligand trap ACE-536 corrects anemia by promoting late-stage erythropoiesis," Nat Med. 20:408-14.
Swaminathan et al. (2013) "Interleukin-27 treated human macrophages induce the expression of novel microRNAs which may mediate anti-viral properties," Biochem. and Biophy. Res. Com. 434:228-34.
Tang et al. (2014) "DNA methylation-mediated epigenetic silencing of miR-720 contributes to leukemogenesis in acute myeloid leukemia," Zhonghua Xue Ye Xue Za Zhi 35:1009-12.
Tang et al. (2015) "MicroRNA-720 promotes in vitro cell migration by targeting Rab35 expression in cervical cancer cells," Cell Biosci. 5:56.
Teruel-Montoya et al. (2014) "MicroRNA Expression Differences in Human Hematopoietic Cell Lineages Enable Regulated Transgene Expression," PloS One 9:e102259.
Wang et al. (2014) "MicroRNA-486 regulates normal erythropoiesis and enhances growth and modulates drug response in CML progenitors," Blood, 125 (8): 1302-1313.
Wang et al. (2015) "Regulation of T cell function by microRNA-720," Sci. Rep. 5:12159.
Wang et al. (2015) "Evaluation of miR-720 prognostic significance in patients with colorectal cancer," Tumour Biol. 36:719-27.
Wong et al. (2013) "Orchestrated Intron Retention Regulates Normal Granulocyte Differentiation," Cell 154:583-95.
Yamasaki et al. (2009) "Angiogenin cleaves tRNA and promotes stress-induced translational repression," J. Cell Biol. 185:35-42.
Yu et al. (2010) "miR-451 protects against erythroid oxidant stress by repressing 14-3-3z," Genes Dev. 24:1620-33.
Zermati et al. (2000) "Transforming growth factor inhibits erythropoiesis by blocking proliferation and accelerating differentiation of erythroid progenitors," Experimental Hematology 28:885-94.
Zhang et al. (2012) "A short linear motif in BNIP3L (NIX) mediates mitochondrial clearance in reticulocytes," Autophagy 8:1325-32.

* cited by examiner pre-miR-4732

SEQ ID NO: 01

977-983 of SMAD2 3' UTR  5'  GCAGUAUAAUUAUUUCAGGGAU  SEQ ID NO: 20
                             ||||||
hsa-miR-4732-3p           3'  GUCUUGUCCUGUCCAGUCCCG   SEQ ID NO: 21
                                              |||
mutated SMAD2 3' UTR      5'  GCAGUAUAAUUAUUUUCACCCAU SEQ ID NO: 22

4934-4940 of SMAD4 3' UTR 5'  UAAUUGCUAGUGUUUUCAGGGAU SEQ ID NO: 23
                                    ||||||
hsa-miR-4732-3p           3'  GUCUUGUCCUGUCCAGUCCCG   SEQ ID NO: 24
                                    |||
mutated SMAD4 3' UTR      5'  UAAUUGCUAGUGUUUUCACCCAU SEQ ID NO: 25

FIG. 4A

NT mimic    miR-4732-3p mimic

SMAD4

1    0.90

SMAD2

1    0.80

α tub

NT ASO    miR-4732-3p ASO

SMAD4

1    4.00

SMAD2

1    2.17

α tub

COMPOSITIONS AND METHODS FOR BLOOD STORAGE

CROSS REFERENCE TO RELATED APPLICATIONS

This application is a U.S. National Phase of International Application No. PCT/US2017/026390, filed on Apr. 6, 2017, which claims the benefit of priority to U.S. Provisional Patent Application Ser. No. 62/318,821 filed on Apr. 6, 2016, the disclosure of each of which is incorporated herein by cross-reference in its entirety.

SEQUENCE LISTING

The sequence listing submitted herewith, entitled "17-312-WO_SequenceListing_ST25.txt" and 6 kb in size, is incorporated by reference in its entirety.

BACKGROUND

Stored red blood cells and other blood products are one of the most prescribed procedures or "drugs" in modern medicine. The global market for blood products reached $23.5 billion in 2012 and is expected to reach $28.8 billion in 2017. In the United States, blood transfusion is one of the commonly performed procedures during hospitalization, and the rate of hospitalization with blood transfusion has more than doubled since 1997.

Additionally, with the increased capacity to detect the drugs and chemicals used for doping to enhance performance, more instances of blood transfusion (allogeneic or autologous), termed "blood doping," have been found in different athletic competitions. While blood doping methods were prohibited by the International Olympic Committee in the 1980s, there is a lack of direct and reliable methods to detect autologous blood transfusions (ABT). Therefore, there is an urgent need for the development of better and novel methods to detect ABT and other forms of blood doping. Since it is not possible to separate the circulating "fresh" vs. transfused "stored" red blood cells (RBCs, also called erythrocytes), most of the current detection methods are indirect by measuring the "response" to the blood transfusion, such as various parameters of erythropoiesis, e.g. hemoglobin (Hb) and erythropoietin (EPO) levels. The "Athletes Biologic Passport" has been developed to monitor several selected RBC parameters over time to identify aberrations and nonphysiologic changes as indicators of ABT. Transfusion of stored blood also leads to "immune" response of leukocytes by the induction of many inflammatory genes such as the leucocyte immunoglobulin receptors, toll-like receptor (TLR) pathway, adaptive immune response and cell death/apoptosis (Pottgiesser et al. (2009) Vox sanguinis 96:333-6). However, these indirect approaches suffer from various complicating factors that reduce the accuracy of the prediction. In addition, these indirect methods cannot detect the ABT events after the disappearance of the host response, resulting in a very short window of detection. Finally, many athletes have learned to minimize the host response through "micro-dosing" to avoid detection of host responses. These issues all point to the current inadequacy of ABT detection and the urgent need for a novel method that relies on the intrinsic differences that occur during the processing and storage of RBCs.

The intention of ABT is often to increase the number of RBCs and improve the oxygen-carrying capacity above physiological levels to enhance athletic performance. During terminal differentiation, RBCs lose their nuclei and are thought to lack any genetic materials, including RNAs. Contrary to this long-held belief, it has been discovered that there are abundant and diverse (>200) species of microRNAs as well as other transcripts in mature RBCs (Chen et al. (2008) *PLoS One* 3:e2360, Sangokoya et al. (2010) *Methods of Molecular Biology* 667:193-203, Rathjen et al. (2006) *FEBS Lett.* 580:5185-8, Friedlander et al. (2008) *Nat Biotechnol.* 26:407-15, LaMonte et al. (2012) *Cell Host Microbe.* 12:187-99, Doss et al. (2015) *BMC Genomics* 16:952). This result has been validated by many different laboratories world-wide.

During the past few years, the protocol has been optimized (Sangokoya et al. (2010) *Methods of Molecular Biology* 667:193-203) to analyze this newly discovered genetic material in sickle cell disease (SCD) RBCs, which in turn has provided a better understanding of its role in anemia severity (Sangokoya et al. (2010) *Blood* 116:4338-48) and malaria resistance (LaMonte et al. (2012) *Cell Host Microbe.* 12:187-99). Illumina sequencing has been used to characterize the small RNA populations in mature RBCs and identified hundreds of known, as well as 27 novel microRNAs (Doss et al. (2015) *BMC Genomics* 16:952). The RBC transcriptome is significantly altered by various treatments (Chen et al. (2008) *PLoS One* 3:e2360). A recent study found that in vitro blood storage led to distinct microRNA gene expression changes in RBCs (Kannan et al. (2010) *Transfusion* 50:1581-8). Such gene expressions induced by particular perturbations can be captured by genomic profiling as "gene signatures" to indicate the presence of such perturbations. It is also possible that in vitro storage may affect the expression of other RBC transcripts, including long noncoding RNA (lncRNA), and various degradation fragments. It is therefore possible to identify genetic signatures of blood storage in transfused RBCs that can then be used as evidence of ABT use by athletes. Furthermore, the storage of RBCs in vitro also leads to increased levels of free microRNA in plasma as the RBC is a major source of circulating microRNAs (McDonald et al. (2011) *Clin Chem.* 57:833-40). These changes can be identified in plasma and blood cells of athletes as signatures of ABT and other forms of blood doping.

The genetic analysis of the RBC transcriptome has several additional benefits for the detection of blood doping. First, the genetic material in the RBC offers extremely rich contents for a much more precise definition of doping as compared to the small number of parameters used in the current blood passport program. These will include both the expression and SNP variations of the RBC transcriptome. Second, as the throughput of next generation sequencing increases exponentially and cost keep dropping, the use of such sequencing analysis will become quite affordable. Third, the RBC transcriptome profiling also captures the changes in response to other doping strategies, such as stimulation of EPO and HIF. Since the life-span of RBCs in healthy individuals is three months, these genetic footprints are likely to persist and be detectable for a long time. The present invention provides several promising RBC "storage signatures" with features of broad tRNA fragmentations. In addition, the whole transcriptome analysis of the RBC was obtained to have the best effective baseline and tools to develop storage signatures. Unexpectedly, an extensive repertoire of long erythrocyte RNAs were uncovered that encode many proteins critical for erythrocyte differentiation and function. Joint analysis of both short and long RNAs identified several loci with co-expression of both microRNAs and long RNAs spanning microRNA precursor regions.

The following studies present the most extensive profiling of erythrocyte RNAs to date, and describes primate-specific interactions between the key modulator miR-4732-3p and TGF-β signaling. These complete transcriptome analyses provides important baseline information and the analytic framework to develop RBC "storage gene signatures." The results also demonstrate that there are significant fragmentations of tRNAs and other RNA species during in vitro storage that result from the activities of angiogenin, a known stress-activated nuclease, that is increased during storage. Described herein are novel "storage signatures" of RBCs with features of broad fragmentations and other changes in transcriptome to detect ABT and blood doping, as well as detecting and preventing deterioration of a RBC storage sample.

SUMMARY OF THE INVENTION

The present disclosure is based, in part, on the changes in the RBC transcriptome (all RNA population) during processing and storage that have significant potential to impact the practice of blood storage, monitoring and handling. Specifically, the inventors have found that dramatic changes in the RBC transcriptome occur during standard RBC processing and storage conditions used in blood banks. These RNA changes can serve as a means to monitor the length of RBC storage, as well as a means to improve and/or monitor the quality of the RBC during this storage.

One aspect of the present disclosure provides a method of detecting autologous blood transfusions (ABT) or blood doping comprising: (a) isolating a blood sample from a subject; and (b) determining the presence of at least one RNA molecule and/or at least one RNase associated with stored blood, wherein differential expression of at least one RNA molecule and/or at least one RNase associated with stored blood indicates the presence of autologous blood transfusions or blood doping.

In some embodiments, the expression of at least one of the RNA molecules is increased. In certain embodiments, the RNA molecule is selected from the group consisting of miR-720, miR-33a-5p and combinations thereof.

In some embodiments, the expression of at least one of the RNA molecules is decreased. In certain embodiments, the RNA molecule is selected from the group consisting of miR-563, miR-582-5p and combinations thereof.

In yet other embodiments, the RNA molecule comprises the RNA molecule having the sequence set forth in any of SEQ ID NO: 31, SEQ ID NO: 32, SEQ ID NO: 33, or SEQ ID NO: 34 and combinations thereof.

In certain embodiments, the RNase comprises an RNase that contributes to the transcriptome changes in the blood sample. In yet other embodiments, the RNase comprises angiogenin.

Another aspect of the present disclosure provides a method of determining the quality of a red blood cell (RBC) storage sample comprising: (a) isolating an aliquot from the storage sample; and (b) determining the presence of at least one RNA molecule and/or at least one RNase associated with storage lesion; wherein differential expression of at least one RNA molecule and/or at least one RNase associated with storage lesion is indicative of poor quality.

In some embodiments, the method is repeated at various time points after storage.

In certain embodiments, the expression of at least one of the RNA molecules is increased. In yet other embodiments, the RNA molecule is selected from the group consisting of miR-720, miR-33a-5p and combinations thereof.

In certain embodiments, the expression of at least one of the RNA molecules is decreased. In yet other embodiments, the RNA molecule is selected from the group consisting of miR-563, miR-582-5p and combinations thereof.

In yet other embodiments, the RNA molecule comprises the RNA molecule having the sequence set forth in any of SEQ ID NO: 31, SEQ ID NO: 32, SEQ ID NO: 33, or SEQ ID NO: 34 and combinations thereof.

In certain embodiments, the RNase comprises an RNase that contributes to the transcriptome changes in the blood sample. In yet other embodiments, the RNase comprises angiogenin.

Another aspect of the present disclosure proves a method of preventing the deterioration of a RBC storage sample comprising: (a) isolating an aliquot from the storage sample; (b) determining the presence of at least one RNA molecule and/or at least one RNase associated with storage lesion; and (c) administering to the storage sample an effective amount of an anti-RNA molecule and/or anti-RNase inhibitor.

In some embodiments, the method is repeated at various time points after storage.

In certain embodiments, the expression of at least one of the RNA molecules is increased. In yet other embodiments, the RNA molecule is selected from the group consisting of miR-720, miR-33a-5p and combinations thereof.

In certain embodiments, the expression of at least one of the RNA molecules is decreased. In yet other embodiments, the RNA molecule is selected from the group consisting of miR-563, miR-582-5p and combinations thereof.

In certain embodiments, the RNA molecule comprises the RNA molecule having the sequence set forth in any of SEQ ID NO: 31, SEQ ID NO: 32, SEQ ID NO: 33, or SEQ ID NO: 34 and combinations thereof.

In certain embodiments, the RNase comprises an RNase that contributes to the transcriptome changes in the blood sample. In yet other embodiments, the RNase comprises angiogenin.

In some embodiments, the anti-RNA molecule and/or anti-RNase inhibitor comprises Ribonuclease/angiogenin inhibitor 1.

Another aspect of the present disclosure provides all that is disclosed and illustrated herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing aspects and other features of the disclosure are explained in the following description, taken in connection with the accompanying drawings, herein:

FIG. 1A. Distribution of total number of expressed transcripts across indicated cell types. A transcript was considered expressed if the RPKM value was ≥0.5. FIG. 1B. GSEA analysis of the top 500 expressed erythrocyte transcripts in the ranked expressed transcripts of the day 8 erythroid progenitor (D8) vs. PBMC samples. FIG. 1C. Distribution of the genomic location for RNA-Seq reads. Locations represent average number of reads for the three RBC, three PBMC, and two erythroid progenitor independent samples. Intronic reads are included if <10 kb upstream of a transcription start site or <10 kb downstream of a transcription end site.

FIG. 2A. Deep sequencing of short RNAs from mature RBCs was performed using the Illumina HiSeq technology. Raw sequences were mapped to the genome, filtered through miRDeep, and categorized. Identified microRNA loci were cross-referenced with miRBase (v. 21) and UCSC Genome Browser (hg 38) to distinguish between candidate novel and known microRNAs. FIG. 2B. Relative percentages (log base 10) of read numbers for top 10 microRNAs among five different samples. Percentages are averages based on total number of known, mature microRNA reads for each sample. FIG. 2C. Relative percentage representation of genomic location for both known and putative microRNAs. Listed genomic locations for mature microRNA sequences are relative to RefSeq annotated transcripts in UCSC genome browser (hg38). For mature microRNA sequences spanning both introns and coding region, or UTR and coding regions of alternative transcripts, sequence is listed in coding region. FIG. 2D. Relative percentage representation of sequence conservation for both known and putative microRNAs. Conservation of mature microRNA sequence indicates exact sequence alignment in listed number of species (from human, chimp, rhesus monkey, dog, mouse, and zebrafish), allowing for up to one base mismatch outside of the microRNA seed sequence (nucleotides 2-8), and no mismatches within the seed sequence.

FIG. 3A. Location, sequence read length, relative read number, and vertebrate conservation of noncoding RNAs within the chromosome 17 miR-144/451 locus according to UCSC genome browser (hg38). Solid lines indicate average read numbers, dotted lines represent highest and lowest standard deviations of read numbers across the samples. The strand orientation of each noncoding RNA is indicated. FIG. 3B. Expression of miR-144-5p, miR-4732-3p, and miR-4732-5p, during CD34+ erythroid differentiation using progenitors from three different individuals. Differentiation is listed from day 6 to day 16. U6 snRNA was used as a loading control, with fold difference set relative to day 6. FIG. 3C. Predicted folding structure for the miR-4732 pre-microRNA according to miRDeep, and frequency of reads for mature microRNAs from one representative sample. The most prevalent mature read sequences for miR-4732-3p (dark grey) and miR-4732-5p (light grey) are shown. FIG. 3D. Sequence conservation of miR-4732-3p in listed species. The nucleotide sequences for the miR-4732-5p reads are: Reads 33 (SEQ ID NO: 02); Reads 19 (SEQ ID NO: 03); Reads 173 (SEQ ID NO: 4). The nucleotide sequences for the miR-4732-3p reads are: Reads 323 (SEQ ID NO: 05); Reads 127 (SEQ ID NO: 06); Reads 394 (SEQ ID NO: 07); Reads 12791 (SEQ ID NO: 08). Primates are listed adjacent to white box, non-primates listed adjacent to black box. Seed sequence is boxed, and base mismatches with human miR-4732-3p are highlighted in grey.

FIG. 4A-4F shows MiR-4732-3p directly regulates SMAD2 and SMAD4. FIG. 4A. Alignment of miR-4732-3p and predicted target sites in the 3' UTR of SMAD2 and SMAD4, with mutated binding sites underlined. FIG. 4B. Relative changes of reporter activities in K562s co-transfected with luciferase constructs and indicated microRNA mimics. A portion the SMAD2 and the SMAD4 3'UTRs were cloned downstream of Renilla in separate psiCheck-2 vectors (n=4) (*p<0.05, p<0.01). FIG. 4C. Relative changes of reporter activities in K562s co-transfected with luciferase constructs and microRNA-blocking antisense oligonucleotides (ASOs) (n=4) (*p<0.001). FIG. 4D. Relative changes of reporter activities in K562s transfected with wild-type (WT) or mutated (MUT) SMAD2 or SMAD4 3'UTR constructs (n=4) (*p<0.05). FIG. 4E. Western blots of SMAD2 and SMAD4 protein expression 24 hours after transfection of K562s with the indicated microRNA mimics. FIG. 4F. Western blots of SMAD2 and SMAD4 protein expression 24 hours after transfection of K562s with the indicated microRNA ASOs. Alpha tubulin was used as a loading control for normalization. Protein desitometric values are listed. The fold change of expression for each treatment group was first normalized to alpha tubulin input for that treatment, then ratio set relative to the control treatment.

FIG. 5A. Relative changes of TGF-β reporter activities in K562 cells co-transfected with luciferase constructs and microRNA mimics (n=4) (**p<0.01). Cells were transfected with microRNA mimic, SMAD4-responsive Firefly construct, and a separate Renilla construct as a transfection control. FIG. 5B. Relative mRNA levels of p21, PAI-1, Bax, and Bim 24 hours after transfection of K562s with microRNA mimics. Levels were determined using qPCR and normalized by GAPDH (n=3) (*p<0.05). FIG. 5C. Total cell number of primary CD34 erythroid progenitors 48 and 72 hours after equal numbers of cells were transfected with indicated microRNA mimics on day 8 of differentiation (n=3) (*p<0.05). FIG. 5D. Total cell number of primary CD34 erythroid progenitors 24 hours after equal numbers of cells were transfected with indicated combinations of microRNA mimics and overexpression constructs on day 8 of differentiation (n=3) (*p<0.05, **p<0.01).

FIG. 7 shows upregulated and downregulated microRNAs during in vitro storage of RBCs.

FIG. 10A. Structure of the qPCR probes: tRNA_1 GGCCCUAUAGCUCAGGGUUAGAGCACUGGU (SEQ ID NO: 27); tRNA_2 CUUGUAAACCAGGGGU-CGCGAG (SEQ ID NO: 28); and tRNA_3 AUCUCGCUGGGGCCUCCA (SEQ ID NO: 29). The black arrows surrounding miR-720 in the top portion of the figure represent the putative cleavage sites to generate mature miR-720; the nucleotides (black) surrounding miR-720 (grey) comprise the miR-720 precursor sequence. The bottom portion of the figure represents nucleotides (black) surrounding miR-720 (grey) in an alternative structure in which the miR-720 sequence is cleaved from a tRNA mimic. FIG. 10B is a graph showing the RNA fragment enrichment during in vitro storage.

DETAILED DESCRIPTION OF THE INVENTION

Figure 1A:
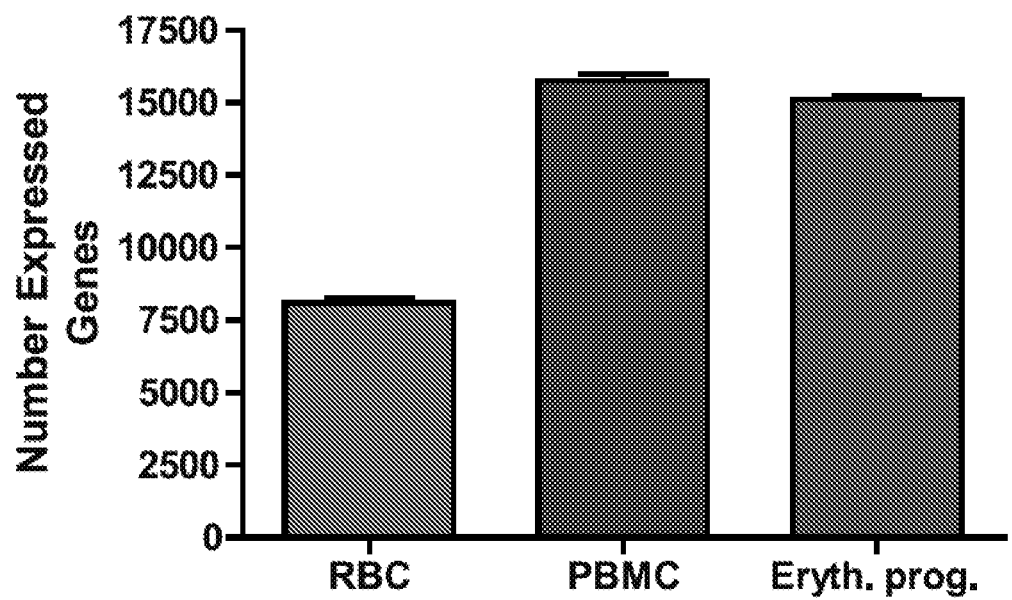
FIG. 1A-1C shows population characteristics of erythrocyte long RNAs.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value can be "slightly above" or "slightly below" the endpoint without affecting the desired result.

Unless otherwise defined, all technical terms used herein have the same meaning as commonly understood by one of ordinary skill in the art to which this disclosure belongs.

As used herein, the term "RNA molecule" refers to any RNA molecule, including, but not limited to, messenger RNA (mRNA), ribosomal RNA (rRNA), signal recognition particle RNA (7SL RNA or SRP RNA), transfer RNA (tRNA), transfer RNA mimics (tRNA mimic) and fragments thereof, transfer-messenger RNA (tmRNA), small nuclear RNA (snRNA), small nucleolar RNA (snoRNA), SmY RNA, small Cajal body-specific RNA (scaRNA), guide RNA (gRNA), ribonuclease P, Ribonuclease MRP, Y RNA, Telomerase RNA component (TERC), spliced leader RNA (SL RNA), antisense RNA (aRNA or asRNA), Cis-natrual antisense transcript (cis-NAT), CRISPR RNA (crRNA), Long noncoding RNA (lncRNA), microRNA (miRNA), Piwi-interacting RNA (piRNA), Small interfering RNA (siRNA), Trans-acting siRNA (tasiRNA), Repeat associated siRNA (rasiRNA), 7SK RNA (7SK), and the like.

As used herein, the term "RNase" refers to any type of nuclease (e.g., ribonuclease) that catalyzes the degradation of RNA into smaller components. RNases include endoribonucleases and exoribonucleases. Examples include, but are not limited to, RNase 5 (angiogenin), RNase A, RNase H, RNase III, RNase L, RNase P, RNase PhyM, RNase T1, RNase T2, RNase U2, RNase V, Polynucleotide Phosphorylase (PNPase), RNase PH, RNase R, RNase D, RNase Tm Oligoribonuclease, Exoribonuclease I and Exoribonuclease II, or other nucleases that contribute to the transcriptome changes during RBC processing and storage. In some embodiments, the ribonuclease comprises angiogenin.

As used herein, the term "biomarker" refers to a naturally occurring biological molecule present in a subject or sample at varying concentrations useful in predicting the risk or incidence of a condition, such as Storage Lesion(s), Autologous Blood Transfusion (ABT) and/or blood doping. For example, the biomarker can be present in higher or lower amounts in the subject or sample as compared to a control. The biomarker can include enzymes, proteins, nucleic acids, ribonucleic acids, or polypeptides. In some embodiments, the biomarker is an RNA molecule and/or combinations of several RNA molecules. In other embodiments, the biomarker comprises an enzyme. In some embodiments, the enzyme comprises an RNase. In some embodiments, the biomarker comprises an RNA molecule that is found in higher levels after blood and/or serum and/or plasma has been stored. In certain embodiments, the RNA molecule comprises miR-720 (SEQ ID NO: 31; Accession No. MIMAT0005954), miR-33a-5p (SEQ ID NO: 32; Accession No. MIMAT0000091) and combinations thereof. In other embodiments, the biomarker comprises an RNA molecule that is found in lower levels after blood and/or serum and/or plasma is stored. In certain embodiments the RNA molecule comprises miR-563 (SEQ ID NO: 33; Accession No. MIMAT0003227), miR-582-5p (SEQ ID NO: 34; Accession No. MIMAT0003247) and combinations thereof. In yet other embodiments, the biomarker comprises an enzyme. In some embodiments, the biomarker comprises an RNase. In certain embodiments, the biomarker comprises angionenin and/or other nucleases found to be altered during storage. It should be appreciated by those skilled in the art that all, some portion thereof, of the RNA molecule and enzymes can be expressed in the sample.

The term "differential expression" or "differential analysis" are used interchangeably herein and refer to, but are not limited to differences in levels for an RNA molecule or an RNase between control and experimental samples. The terms refer to a set of at least one RNA molecule or at least one RNase, where the level of the individual RNA molecule/s or RNase differs between a first physiological state or condition relative to their expression level in a second physiological state or condition, for example, between a fresh RBC sample and a stored RBC sample. In addition, the terms are used herein refer to the levels of an RNA molecule or an RNase at greater or lesser amounts in an storage blood and/or serum and/or plasma sample than the levels of an RNA molecule or an RNase in a fresh blood and/or serum and/or plasma sample from the same subject or a different subject. For example, the terms include comparisons of levels between an RNA molecule or an RNase in a sample of RBC obtained at day 0 (or in a "fresh" sample) and an RNA molecule or RNase in an RBC storage sample obtained at any time point between days 1 and 42. Differential expression of an RNA molecule or RNase includes increased levels and decreased levels of an RNA molecule or RNase. An example of increased levels of RNA molecules in an RBC storage sample is demonstrated herein for miR-720 and miR-33a-5p, as discussed more fully below. An example of decreased levels of RNA molecules in an RBC storage sample is demonstrated herein for miR-563 and miR-582-5p, as discussed more fully below. An example of increased levels of an RNase in an RBC storage sample is demonstrated herein for angiogenin, as discussed more fully below.

As used herein, the term "storage-specific signature" refers to a set of at least one RNA molecule, where the level of the individual RNA molecule/s or RNase differs between a first physiological state or condition relative to their expression level in a second physiological state or condition, for example, between a fresh RBC sample and a stored RBC sample.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like.

The term "sample" as used herein includes, but is not limited to, a sample containing tissues, cells, and/or biological fluids isolated from a subject. Examples of biological samples include, but are not limited to, tissues, cells, biopsies, blood, lymph, serum, plasma, urine, saliva, mucus and tears. In one embodiment, the biological sample is a biopsy (such as a tumor biopsy). A biological sample can be obtained directly from a subject (e.g., by blood or tissue sampling) or from a third party (e.g., received from an intermediary, such as a healthcare provider or lab technician). In some embodiments, the sample comprises blood and/or serum and/or plasma.

The term "aliquot" as used herein refers to a portion of a larger whole, especially a sample taken for chemical analysis or other treatment. For example, for purposes of determining the quality of or preventing the deterioration of a red blood cell storage sample, an aliquot of blood can be removed from an RBC storage sample to be analyzed.

As used herein, the term "angiogenin inhibitor" refers to any compound or composition that is capable of inhibiting the expression and or function of angiogenin. Inhibitors include, but are not limited to, antibodies, antisense RNA, cDNA, peptides, small molecules, oligonucleotides and the like. In some embodiments, the angiogenin inhibitor comprises Ribonuclease/angiogenin inhibitor 1 (RNH1) or any compounds that reduce the angiogenin activities.

As used herein, the term "RNA molecule inhibitor" refers to any compound or composition that is capable of inhibiting the expression and/or function of an RNA molecule. Inhibitors include, but are not limited to, antibodies, antisense RNA, cDNA peptides, small molecules, oligonucleotides, and the like.

The modern day practice for red cell storage is to purify and wash the red cells, then store the red cells in media specific for storage. Most of the quality controls for red cell storage are specifically designed to detect, and remove infected blood products. Red cells are stored at 4° C. for up to 6 weeks before being discarded. Relative little attention is paid to understanding the changes within red cells during storage as a method of quality control, specifically to compare the quality of red cells at different time points. In addition, the transfusion of "old" (stored for extended period of time) stored red cells have been found to be associated with various adverse clinical outcomes. However, it remains unclear what changes in red cells during storage account for the adverse effects caused by the "old" blood.

The present disclosure describes, in part, transcriptomic changes in red blood cells (RBC) during storage have significant potential to impact the practice of blood storage, monitoring as well as handling. Specifically, the Inventors have found a dramatic increase in tRNA mimic fragments during standard storage conditions. These tRNA fragments can therefore serve as a novel approach to monitor the length of red cell storage, as well as the quality of the red cells during this storage. Similar RNA fragments derived from tRNAs have been shown to have significant biological activities and likely contribute to "storage lesions" associated with red cells which have been stored for extended periods of time.

Accordingly, one aspect of the present disclosure provides a method of determining the quality of a red blood cell (RBC) storage sample comprising, consisting of, or consisting essentially of: (a) isolating an aliquot from the RBC storage sample; (b) determining the presence of at least one RNA molecule and/or at least one RNase associated with storage lesion, wherein differential expression of at least one RNA molecule and/or at least one RNase is indicative of poor quality.

As used herein, the term "isolating" refers to obtaining an aliquot or sample of blood from either a RBC storage sample or directly from a subject. Methods of isolating an aliquot or sample of blood from an RBC storage sample include but are not limited to, removing the blood anaerobically via a sterile-docking device fitted with a valve to ensure there is no re-entry of air, or other contamination, into the RBC unit. Methods of isolating blood from a subject include, but are not limited to, piercing the skin, by drawing blood out of a vein, or by obtaining a sample of tissues, cells, biopsies, blood, lymph, serum, plasma, urine, saliva, mucus and tears.

As used herein, the term "storage lesion" refers to a collection of changes in the red blood cells that occur during in vitro storage, including but not limited to, the loss of red cell integrity, red cell membrane loss, or hemolysis. These "storage lesion" contribute to the poor clinical outcomes of patients who received transfusion of RBCs which have been stored for extended periods of time.

As used herein, the term "poor quality" or "poor integrity" are used herein interchangeably to refer to an RBC storage sample that has reduced potency, has been compromised, would have potential adverse effects on recipients, or is not suitable for use in blood transfusions or research.

Furthermore, the data provided herein provides preliminary evidence for the role of angiogenin or other RNase(s) in fragmentation of tRNAs during storage. Many studies have indicated the potential functional properties of these tRNA fragments. Therefore, the inhibitors of angiogenin and other responsible nuclease have value in blocking tRNA fragmentation to reduce tRNA fragmentation and undesirable outcomes from the storage lesions.

Another aspect of the present disclosure provides a method of preventing the deterioration of an RBC storage sample comprising, consisting of, or consisting essentially of: (a) isolating an aliquot from the storage sample; (b)

determining the presence of at least one RNA molecule and/or at least one RNase associated with storage lesion; and (c) administering to the sample an effective amount of an anti-RNA molecule and/or anti-RNase inhibitor.

In some embodiments, the sample can be taken at various times between the placement in storage (day 0) or at the end of the typical 6 week period (day 42). For example, samples can be taken for analysis at least once a day every day over a period of 42 days. In other embodiments, sample are taken for analysis at day 1, day 3, day 7, day 14, day 21, day 28, day 35 and day 42. In certain embodiments, samples are taken at least at day 7, day 11, day 14, day 18, and day 21, with evidence showing RNA molecule expression to begin at or around day 14.

In other embodiments, the expression of the RNA molecule is increased. In certain embodiments, the RNA molecule is selected from the group consisting of miR-720, miR-33a-5p and combinations thereof. As described herein, miR-720 is a fragment of the threonine tRNA mimic.

In yet other embodiments, the expression of the RNA molecule is decreased. In certain embodiments, the RNA molecule is selected from the group consisting of miR-563, miR-582-5p and combinations thereof.

In other embodiments, the expression of the RNA molecule comprises the RNA molecule having the sequence set forth in any of SEQ ID NO: 31, SEQ ID NO: 32, SEQ ID NO: 33, or SEQ ID NO: 34 and combinations thereof.

In other embodiments, the RNase comprises angiogenin or other nucleases responsible for the tRNA fragmentation.

The methods described herein are also valuable within the athletic community. Increasing instances of blood transfusion (allogeneic or autologous), termed "blood doping", have been found as "performance enhancing" means in different athletic competitions. With this in mind, there is a need to detect this method of enhancing performance. While blood doping methods were prohibited by the International Olympic Committee starting in the 1980s, there is a lack of direct and reliable methods to detect autologous blood transfusions (ABT). The intention of ABT is to increase the number of red blood cells (RBCs) and improve the oxygen carrying capacity above physiological levels to enhance athletic performance. Most blood transfusions are performed to increase the level of RBCs in the body. During terminal differentiation, RBCs lose their nuclei and are thought to lack any genetic materials. Contrary to this long held belief, RBCs in fact contain abundant and diverse species of microRNAs, as well as other longer RNAs in mature RBCs. During the past few years, the protocol has been optimized to analyze these newly discovered genetic materials in sickle cell disease (SCD) RBCs, which in turn has provided a better understanding of their role in anemia severity, as well as malaria resistance. Illumina sequencing has also been utilized to characterize the small RNA populations in mature RBCs and identified hundreds of known and novel microRNAs. These varied gene expression profiles associated with particular perturbations can be captured by genomic profiling as "gene signatures" to indicate the presence of such perturbations. It is also possible that in vitro storage can affect the expression of other RBC transcripts, including long noncoding RNA (lncRNA), and various degradation fragments. It is therefore possible to identify genetic signatures of blood storage in transfused RBCs that can then be used as evidence of ABT use by athletes. Furthermore, the storage of RBCs in vitro can also lead to increased levels of free microRNA in blood plasma as the RBC is a major source of circulating microRNAs. These changes can be identified in the plasma and blood cells of the athletes as signatures of ABT and other forms of blood doping.

Hence, another aspect of the present disclosure provides a method of detecting autologous blood transfusions (ABT) or blood doping comprising, consisting of, or consisting essentially of: (a) isolating a blood sample from a subject; (b) determining the presence of at least one RNA molecule and/or at least one RNase associated with stored blood, wherein the differential expression of at least one RNA molecule and/or at least one RNase associated with stored blood indicates the presence of autologous blood transfusions or blood doping.

In other embodiments, the expression of the RNA molecule is increased. In certain embodiments, the RNA molecule is selected from the group consisting of miR-720, miR-33a-5p and combinations thereof.

In yet other embodiments, the expression of the RNA molecule is decreased. In certain embodiments, the RNA molecule is selected from the group consisting of miR-563, miR-582-5p and combinations thereof.

In other embodiments, the expression of the RNA molecule comprises the RNA molecule having the sequence set forth in any of SEQ ID NO: 31, SEQ ID NO: 32, SEQ ID NO: 33, or SEQ ID NO: 34 and combinations thereof.

In other embodiments, the RNase comprises an RNase that contributes to the trascriptome changes. In certain embodiments, the RNase comprises angiogenin Another aspect of the present disclosure provides all that is disclosed and illustrated herein.

The following examples are provided as illustration and not by way of limitation.

Example 1: Global Profiling of RBC MicroRNAs During In Vitro Storage

To obtain the whole erythrocyte transcriptome analysis of the RBC to have the best effective baseline and tools to develop storage signatures, high-throughput sequencing was used to identify both short (~18-24 nt) and long (>200 nt) RNAs in mature erythrocytes. (Doss et al. (2015) *BMC Genomics* 16:952) at the baseline before storage. Human erythrocytes are terminally differentiated, anucleate cells long thought to lack RNAs. However, it has previously been shown that many small-sized RNAs persist in erythrocytes.

Cell Sorting, Purification, and RNA Isolation:

Blood was kept on ice after a single draw and was processed within 30 minutes of sample acquisition. For isolation of erythrocytes from whole blood, blood samples were processed as previously described (Pimentel et al. (2014) *Nucleic Acids Research* 42:4031-42). Briefly, a portion of whole blood was washed three times with PBS, centrifuged, and plasma and buffy coat removed. Leukocytes were then depleted from the sample using a Purecell® Leukocyte Reduction Filtration System. Reticulocytes (immature red blood cells) were removed in the CD71 positive fraction using CD71 microbeads with the autoMACS® Separator (Miltenyi Biotec, Bergish Gladbach, Germany). For confirmation of RBC purity after magnetic bead sorting, a CD71-PE antibody (Miltenyi Biotec, Bergish Gladbach, Germany) was used. Flow cytometry was run on the BD FACSCantoII system using the FACSDiva software. All additional flow cytometric analyses were performed using the FlowJo (v.7.6.4) software. For isolation of PBMCs, a buffy coat was separated from whole blood using a Ficoll-Paque (GE Healthcare, Little Chalfont, United Kingdom) centrifugation gradient, and remaining erythrocytes were lysed using a red cell lysis buffer (Qiagen, Hilden, Germany). Total RNA was isolated using the mirVANA miRNA isolation kit (Ambion, Silver Spring, Md., United States).

RNA Library Preparation and Sequence Analysis:

To prepare long RNA-Seq libraries, 1 µg of purified total input RNA was used with the TruSeq Stranded Total RNA Sample Prep Kit with Ribo-Zero Globin (Illumina, San Diego, Calif., United States). A total of 100 ng of erythrocyte RNA was used to prepare short RNA-seq libraries with the TruSeq Small RNA Sample Prep Kit (Illumina, San Diego, Calif., United States). Total RNA-seq and small RNA libraries were separately pooled and analyzed using the Illumina HiSeq 2000 sequencing system. All reads for total RNA-seq and small RNA-seq were sorted based on quality, and raw sequences with removed 3' linker sequences were obtained in FASTQ format. All primary sequencing data are publicly available through the Gene Expression Omnibus (GEO dataset GSE63703). For long RNA-seq, the RNA-seq data was processed using the TrimGalore toolkit to trim low quality bases and Illumina sequencing adapters from the 3' end of the reads. Only pairs where both reads were 20 nt or longer were kept for further analysis. Reads were mapped to the GRCh37r73 version of the human genome and transcriptome (Kilberg et al. (2009) *Trends Endocrinol Metab.* 20:436-43) using the STAR RNA-seq alignment tool (Yamasaki et al. (2009) *J Cell Biol.* 185:35-42). Reads were kept for subsequent analysis if they mapped to a single genomic location. RNA-Seq quality control, genomic position summary statistics, and gene body coverage statistics were generated with the RSeQC toolkit (Emara et al. (2010) *J. Biol. Chem.* 285:10959-68). Gene expression in reads per million per kilobase (RPKM) value were calculated using the cufflinks algorithm (Ivanov et al. (2011) *Mol. Cell.* 43:613-23). Genes that had an RPKM value ≥0.5 in at least one sample were kept for subsequent analysis. Short RNA-seq bioinformatic analyses were performed using miRDeep2 and in house Perl scripts, with methods similar to that previously described (Patrick et al. (2010) *Genes Dev.* 24:1614-9). Gene set enrichment analysis (GSEA) (Sarachana et al. (2015) *Transfusion* 55:2672-83) was computed using the top 500 genes expressed in RBCs as the 'gene set', and the log 2-fold-change of the D8/PBMC samples as the input list to test for the enrichment of top RBC expressing transcripts against those more specific to D8 samples or the PBMC samples.

Results:

Analysis of the short RNA transcriptome with miRDeep identified 287 known and 72 putative novel microRNAs. Unexpectedly, an extensive repertoire of long erythrocyte RNAs that encode many proteins critical for erythrocyte differentiation and function were also uncovered. Additionally, the erythrocyte long RNA transcriptome is significantly enriched in the erythroid progenitor transcriptome. Joint analysis of both short and long RNAs identified several loci with co-expression of both microRNAs and long RNAs spanning microRNA precursor regions. Within the miR-144/451 locus previously implicated in erythroid development, unique co-expression of several primate-specific noncoding RNAs were observed, including a lncRNA, and miR-4732-5p/-3p. miR-4732-3p targets both SMAD2 and SMAD4, two critical components of the TGF-β pathway implicated in erythropoiesis. Furthermore, miR-4732-3p represses SMAD2/4-dependent TGF-β signaling, thereby promoting cell proliferation during erythroid differentiation. This study presents the most extensive profiling of erythrocyte RNAs to date, and describes primate-specific interactions between the key modulator miR-4732-3p and TGF-β signaling during human erythropoiesis. (Doss et al. (2015) *BMC Genomics* 16:952).

To extensively profile the complete transcriptome of mature RBC, highly purified erythrocytes from healthy donors was obtained. As previously described (Sangokoya et al. (2010) *Methods in Molecular Biology* 667:193-203), blood samples were leukocyte-depleted, separated using a density gradient, and CD71– mature erythrocytes were magnetically-selected. Total RNA was isolated, including small-sized RNA, and constructed sequencing libraries for both short (18-24 nt) and long (>200 nt) RNAs from erythrocyte RNA samples. RNA from five individuals was used for erythrocyte short RNA-seq, and RNA from three individuals was used for erythrocyte long RNA-seq. Additionally, total RNA was isolated from peripheral blood mononuclear cells (PBMCs) of three individuals, and RNA from in vitro differentiating CD34+ erythroid progenitors (Day 8 of differentiation) of two individuals. RNA from these nucleated erythroid and peripheral blood mononuclear cells was isolated and used to prepare strand-specific long RNA-seq libraries to compare with the transcriptome of erythrocytes. For long RNA-seq, hemoglobin and ribosomal RNAs were first depleted from the sample, then barcoded sequencing libraries were generated using random primers. The sequencing libraries were pooled and 50 bp paired-end sequencing was performed using the Illumina HiSeq 2000 system. Sequencing unexpectedly identified a large, diverse repertoire of long RNAs in erythrocytes.

To determine both shared and unique aspects of the erythrocyte transcriptome, the erythrocyte transcriptome was compared with that of the PBMC and CD34+ erythroid progenitor transcriptomes. Libraries from these nucleated cells were prepared and run in parallel to that of the erythrocyte long RNA sequencing samples. Using the same analytic methodology and threshold (RPKM of ≥0.5), it was found that mature erythrocytes had far fewer expressed genes (~8092 genes) than other nucleated blood cells such as PBMCs (~15743 genes) and erythroid progenitors (~15113 genes) (FIG. 1A). However, mature erythrocytes still have thousands of transcripts that can provide unique insights into erythroid biology.

Figure 1B:
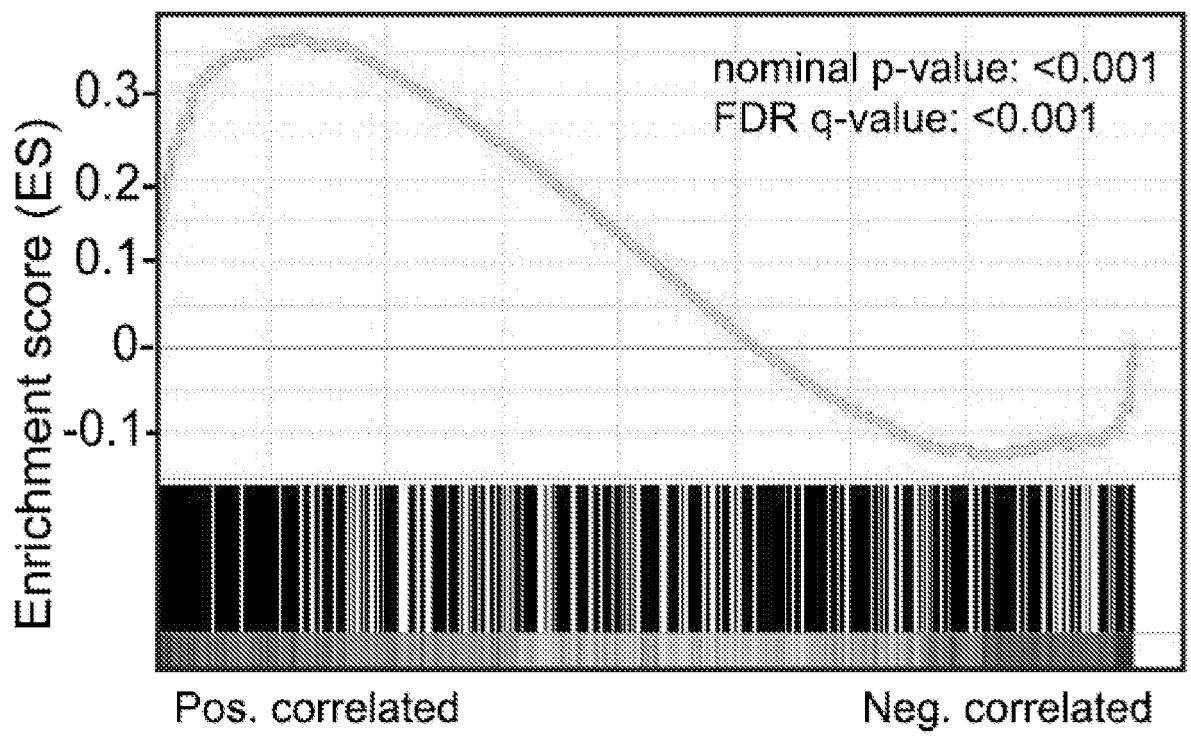

To determine whether the long RNA erythrocyte transcriptome reflects that of erythroid progenitors versus PBMCs, GSEA (Gene Set Enrichment Analysis) was used to determine the relative enrichment of the top 500 erythrocyte RNA transcripts in the day 8 erythroid progenitor (D8) vs. PBMC samples. A highly significant enrichment of the top 500 erythrocyte transcripts in the erythroid progenitor transcriptome was observed (FIG. 1B). Together, these data show selective retention of many long RNAs previously transcribed in nucleated erythrocyte progenitors, consistent with the possibility the erythrocyte RNAs were derived from erythroid precursors.

Figure 1C:
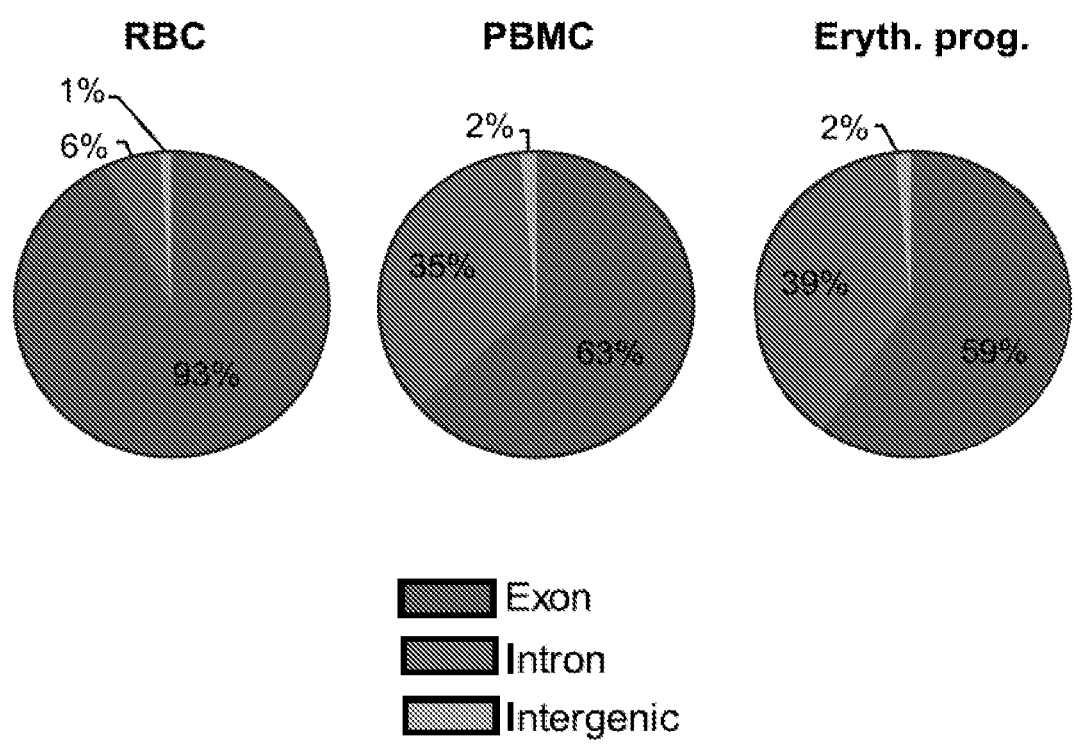

Recent studies have suggested that intron retention and nonsense mediated decay can contribute to degradation of most transcripts during terminal differentiation of granulocytes (Wong et al. (2013) *Cell* 154:583-95) and erythrocytes (Pimentel et al. (2014) *Nucleic Acids Research* 42:4031-42). Therefore, the relative distribution of gene mapping regions for erythrocyte long RNAs were analyzed. On average, 93% of human erythrocyte long RNAs map to annotated exons of coding and noncoding RNAs, far higher than that of PBMCs (63%) and erythroid progenitors (59%) (FIG. 1C). Therefore, compared with nucleated cells, relatively few erythrocyte transcripts map to introns and intergenic regions. This difference reflects that nucleated cells, when compared with anucleate erythrocytes, retain more unprocessed RNAs in the nucleus. Slightly less coverage at the 3' of erythrocyte transcripts was observed, compared to that of PBMC and erythroid progenitor transcripts. Additionally, when the top 500 highest expressed erythrocyte genes were examined for GO (gene ontology) enrichment, significant enrichment in pathways of cellular, protein and macromolecule biosynthesis and metabolisms, defense response, and protein ubiquitination was found.

Next, the most abundant transcripts were examined to obtain insights into erythroid biology. Several of the most highly expressed RNAs are Y RNAs or different components of ribonucleoprotein complexes that represent persistent expression after terminal differentiation. Many of the highest expressed genes in the erythrocyte transcriptome also encode proteins highly relevant for erythroid cell differentiation. For example, BNIP3L mediates mitochondrial clearance during reticulocyte terminal differentiation (Zhang et al. (2012) *Autophagy* 8:1325-32). Abundant SLC25A37 encodes mitoferrin-1, an essential iron importer for the synthesis of mitochondrial heme and iron-sulfur clusters in erythroblasts (Shaw et al. (2006) *Nature* 440:96-100), and FLT encodes the ferritin light chain, a major component of intracellular iron storage (Ponka, et al. (1998) *Seminars in Hematology*, 35:35-54). Another top expressed gene, EPB41, constitutes the red cell membrane cytoskeletal network, which plays a critical role in erythrocyte shape and deformability (Conboy et al. (1986) *Proc. Natl. Acad. Sci. USA* 83:9512-6).

In addition, several highly expressed erythrocyte transcripts encode proteins with known functions previously not associated with erythrocytes. For example, ADIPOR1 encodes the cellular receptor for adiponectin, a hormone secreted by adipocytes that regulates fatty acid catabolism and glucose levels. Interestingly, Japanese individuals with anemia present significantly higher serum levels of adiponectin that that of unaffected individuals, yet the function of such an association remains unknown (Kohno et al. (2014) *European Journal of Haematology* 92:298-307). Highly expressed TMEM56 (Transmembrane protein 56) and OAZ1 (Ornithine Decarboxylase Antizyme 1) also have undiscovered roles in erythroid biology.

Thus, these results demonstrate that when freshly isolated, human RBC have a large number of microRNAs as well as mRNAs and lncRNAs that reveal the unexpected rich genetic contents of the human RBC. These genetic materials can provide an entirely new dimension to our understanding of RBCs in physiological and pathological adaptations.

Figure 2A:
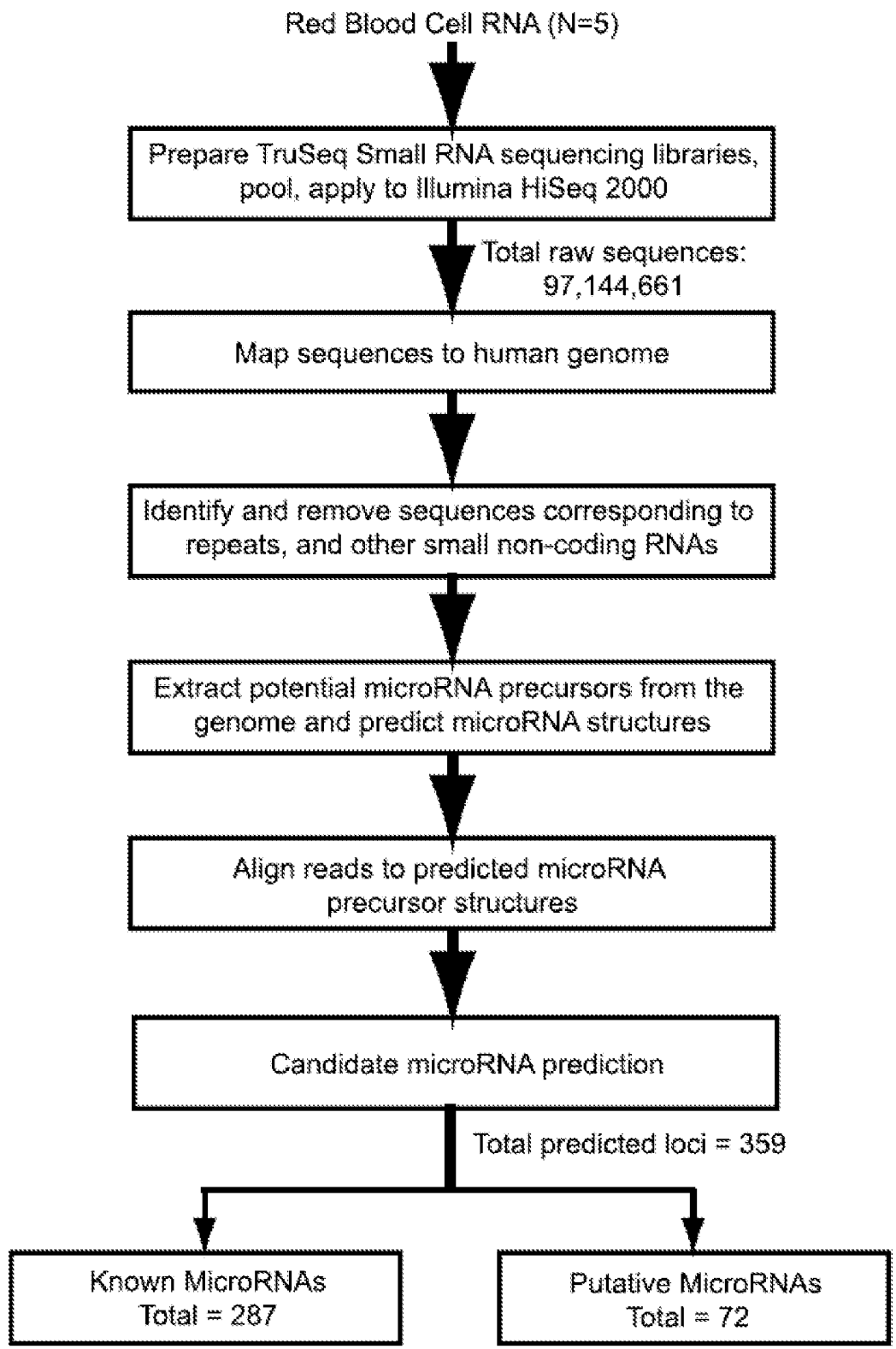
FIG. 2A-2D shows the microRNA identification pipeline and microRNA population characteristics.

Example 2: Mature Erythrocytes Contain a Diverse Repertoire of Known and Putative Novel MicroRNAs In parallel with long RNAs, short (18-24 nt) RNA species from five erythrocyte samples were also sequenced. The short RNA libraries were constructed, pooled, and then applied to the Illumina HiSeq 2000 to generate a total of 97,144,661 reads. To discover small-sized RNAs with microRNA-like characteristics, the miRDeep2 pipeline was employed (Friedlander et al. (2012) *Nucleic Acids Research* 40:37-52) (FIG. 2A), a widely used (Swaminathan et al. (2013) *Biochem. and Biophy. Res. Com.* 434:228-34, Sharbati et al. (2010) *BMC Genomics* 11:275) probabilistic model algorithm based on canonical microRNA precursor processing, and is therefore not limited to previously annotated or highly conserved microRNAs.

Figure 2B:
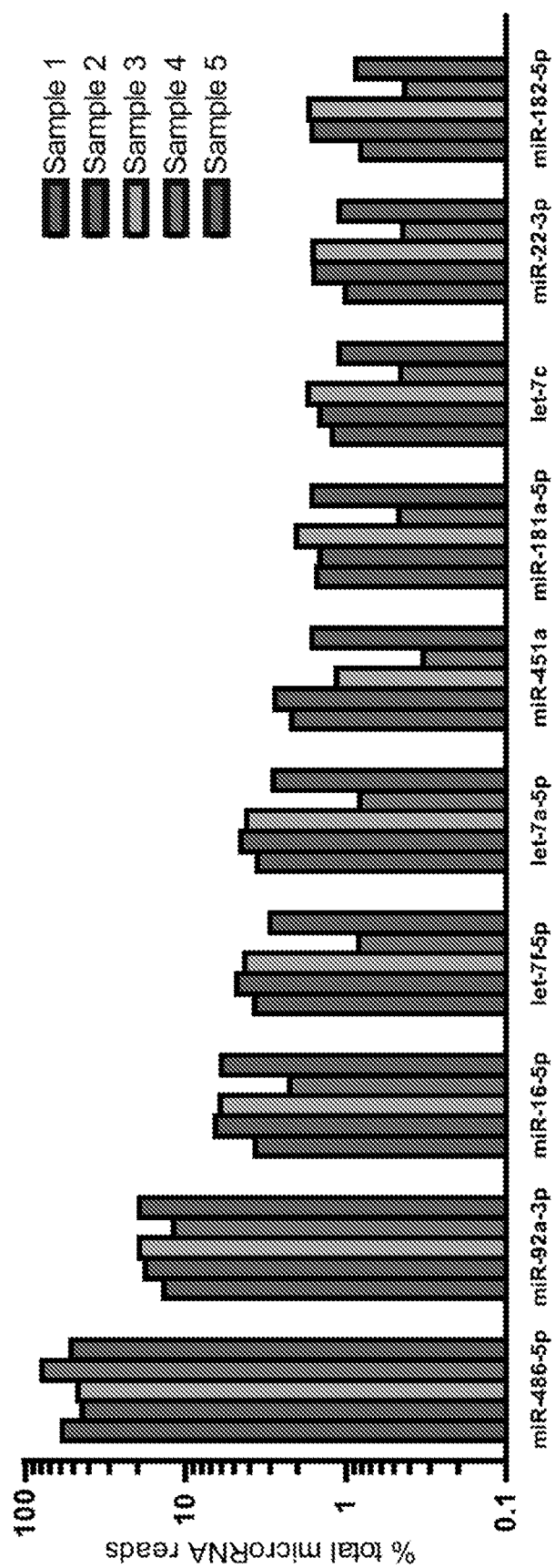

A cutoff for microRNAs based on a miRDeep score of ≥1, and ≥20 reads in at least one sample was employed, like that previously used (Jima et al. (2010) *Blood* 116:e118-27). In all, 359 microRNAs were identified. For the top 10 identified microRNAs, similar percentages of reads were found in all five erythrocyte samples (FIG. 2B), indicating reproducible expression of the most highly expressed microRNAs. Several of the most abundant microRNAs in the dataset were previously shown to be enriched in human erythrocytes, thus validating the findings. For example, the most abundant microRNA, miR-486-5p, accelerates erythroid differentiation (Wang et al. (2014) *Blood*), and its overexpression was associated with an erythroid-like subtype of megakaryocytic leukemia (Shaham et al. (2014) *Blood*). MiR-451a and miR-144-3p are both GATA-1-responsive microRNAs unregulated during erythroid differentiation and play important roles in the anti-stress capacity of erythrocytes (Sangokoya et al. (2010) *Blood* 116:4338-48, Dore et al. (2008) *Proc. Natl. Acad. Sci. USA* 105:3333-8, Yu et al. (2010) *Genes Dev.* 24:1620-33, Fu et al. (2009) *Blood* 113:1340-9, Patrick et al. (2010) *Genes Dev.* 24:1614-9, Byon et al. (2014) *Experimental Hematology*. Additionally, miR-16, miR-92a, and the let-7 family of microRNAs are all among the most abundant erythrocyte microRNAs from previous studies (Chen et al. (2008) *PLoS One* 3:e2360, Noh et al. (2009) *J. Transl. Med.* 7:98, Teruel-Montoya et al. (2014) *PloS One* 9:e102259). Importantly, high plasma levels of miR-486-5p, miR-92a, miR-16 and miR-451a are associated with increased red cell hemolysis in human plasma samples, consistent with their high abundance in erythrocytes (Kirschner et al. (2011) *PloS One* 6:e24145, Pritchard et al. (2012) *Cancer Prevention Research* 5:492-7). Hence, these sequencing data identified a large number of erythrocyte microRNAs. While most of these microRNAs were previously associated with erythrocytes, several abundant microRNAs, such as miR-182-5p, have not been previously associated with erythroid cells.

Figure 2C:
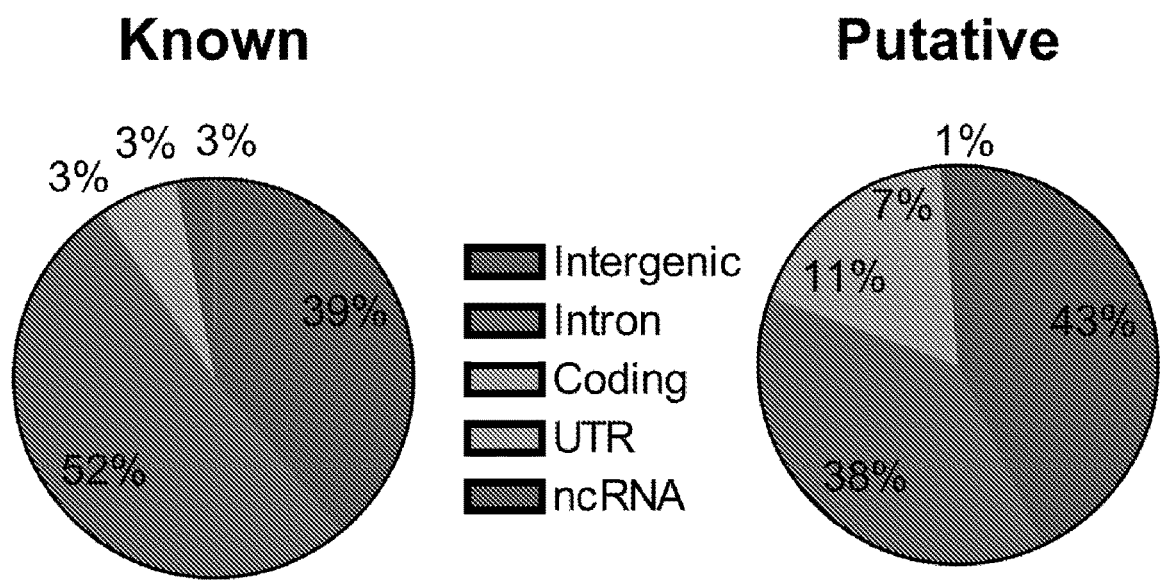
Figure 2D:
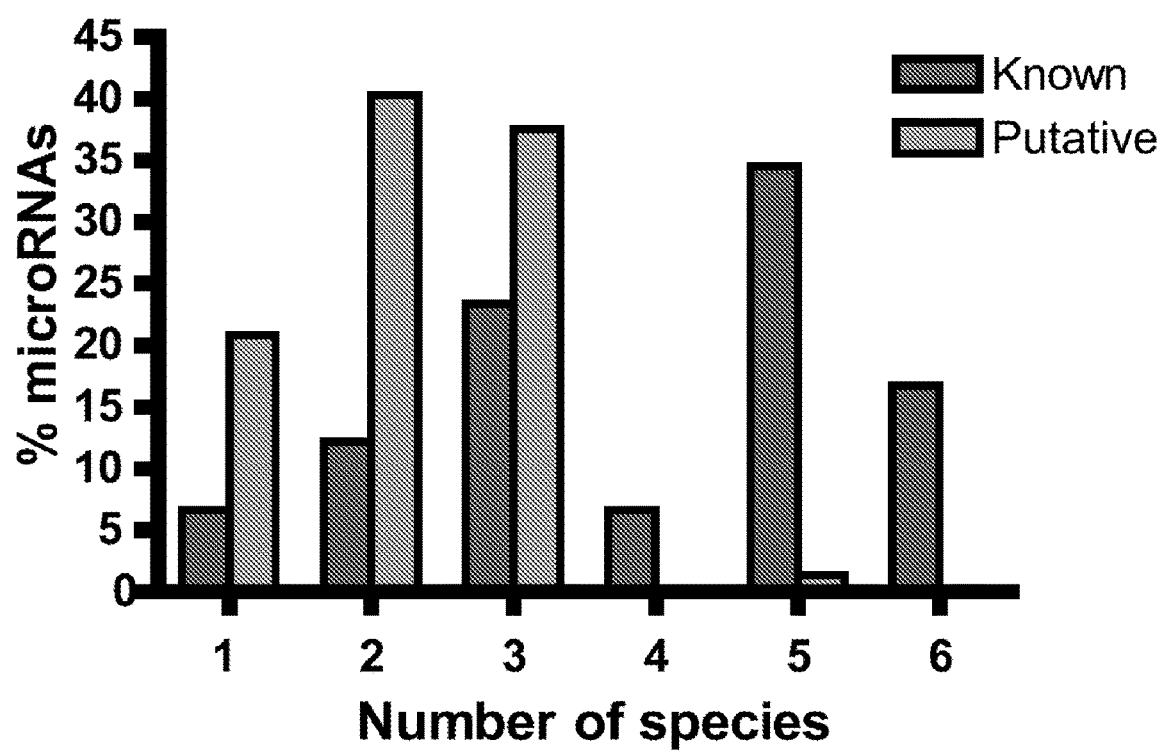

The putative microRNAs identified by miRDeep were further manually annotated and curated using both the UCSC genome browser (hg38) and miRBase (v.21). These analyses lead to 72 putative unannotated microRNAs, and selected microRNA sequences that met criteria for putative microRNAs are shown. The relative genomic location and sequence conservation for both known and putative erythrocyte microRNAs was then determined. The majority of both known (91%) and putative (81%) microRNAs mapped to intergenic or intronic regions, with few microRNAs mapped to coding, untranslated, or long ncRNA regions (FIG. 2C). These results indicate that overall, newly identified putative erythrocyte microRNAs reside in similar genomic regions to that of known microRNAs. The evolutionary conservation was examined of both known and putative microRNAs across six species (human, chimp, rhesus monkey, dog, mouse, and zebrafish) by the number of species in which each full, mature microRNA sequence was found (FIG. 2D). Known microRNAs were identified in more species (4-6 species) than putative microRNAs (1-3 species), and were therefore more conserved. Additionally, most putative microRNA sequences (99%) were only identified in primates, while far fewer known microRNAs were only identified primates (42%). This disparity highlights the utility of miRDeep to identify putative microRNAs that are mostly primate-specific.

Figure 3A:
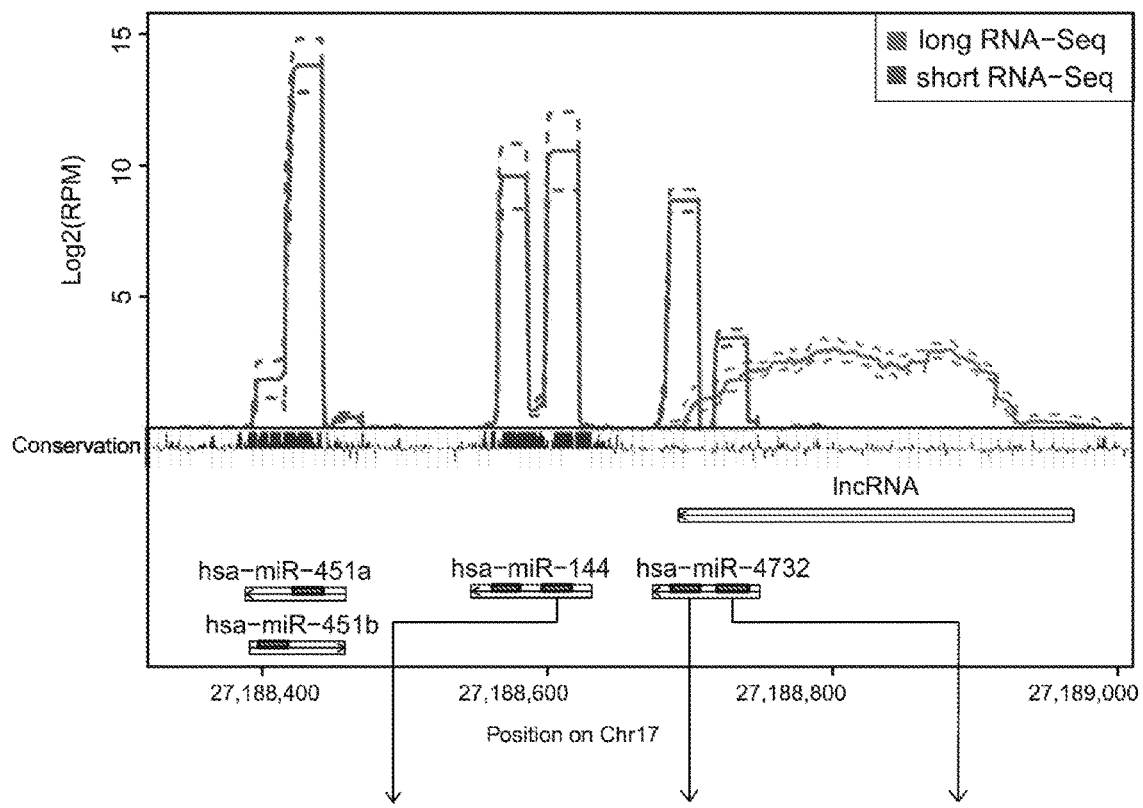
FIG. 3A-3D shows the genomic locations and expression dynamics of noncoding RNAs in the miR-144/451 locus.

Example 3: Joint Analysis of Erythrocyte Long and Short RNA Transcriptomes Reveals Novel Elements within the mIR-144/451 Locus Next, a joint analysis of the long and short RNA erythrocyte transcriptomes was performed. Long and short RNAs that map to adjacent regions were identified. Several long RNA transcripts that spanned different annotated pre-microRNA loci were identified. Together, three instances of co-expression were observed for both erythrocyte microRNAs and long RNAs spanning pre-microRNA loci. There are two distinct patterns of co-expression. In the first pattern, co-expression of both microRNAs and long RNA transcripts spanning entire pre-microRNAs was observed, including 5' and 3' flanking regions in two loci (miR-6087 and miR-3687). In the second pattern, co-expression a long RNA spanning only the 5' portion of the miR-4732 pre-microRNA, proximal to the miR-144/451 region was observed; this lncRNA was confirmed via RT-PCR. Further research focused on the co-expressed microRNAs and the long RNA within the miR-144/451 locus for several reasons (FIG. 3A). This locus has been widely implicated in erythropoiesis, and all RNAs in this locus contain a much higher coverage (>50 reads) than that of RNAs in other co-expression loci. Interestingly, it was found that when the sequencing reads were mapped to the miR-144/451 locus, several RNA reads mapped to distinct elements 5' of pre-miR-144. These RNAs include a ~250 nt lncRNA spanning the 5' hairpin region of pre-miR-4732, as well as miR-4732-5p and -3p (FIG. 3A).

Figure 3B:
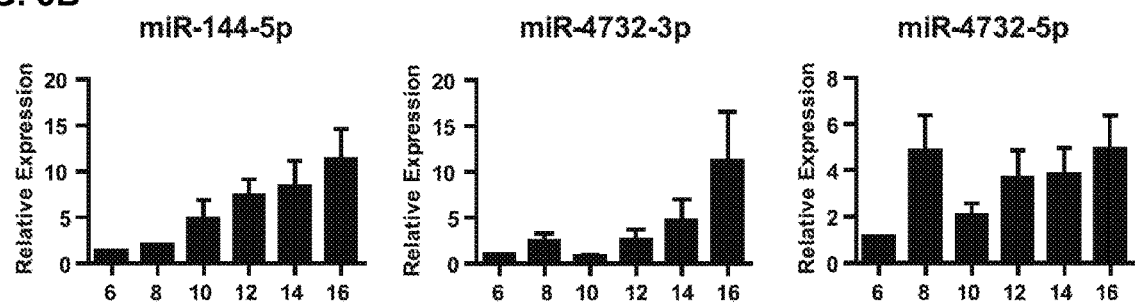

Among the newly identified erythrocyte RNAs, the functional role of miR-4732-3p was investigated for several reasons. First, both miR-4732-5p and -3p were previously uncharacterized. Second, miR-4732-3p is much more highly expressed than miR-4732-5p. Additionally, proximal microRNAs miR-451a and miR-144-3p are significantly induced during erythroid differentiation (Dore et al. (2008) *Proc. Natl. Acad. Sci. USA* 105:3333-8). Real-time PCR was used to determine the expression dynamics of miR-4732-3p and other erythrocyte microRNAs at different time points during in vitro differentiation of CD34+ erythroid progenitors (FIG. 3B). Similar to miR-451a and miR-144-3p (Dore et al. (2008) *Proc. Natl. Acad. Sci. USA* 105:3333-8), both miR-144-5p and miR-4732-3p were also upregulated during erythropoiesis (FIG. 3B). However, miR-4732-5p levels were less dramatically upregulated during erythropoiesis. Additionally, miR-486-5p was upregulated and miR-221 was downregulated during differentiation, as previously described (Wang et al. (2014) *Blood*, Bruchova et al. (2007) *Experimental Hematology* 35:1657-67), indicating successful differentiation of our in vitro erythroid culture. Upregulation of miR-4732-3p, as well as its physical proximity to the miR-144/451 locus suggests its similar regulation and functional role during erythroid development.

Figure 3C:
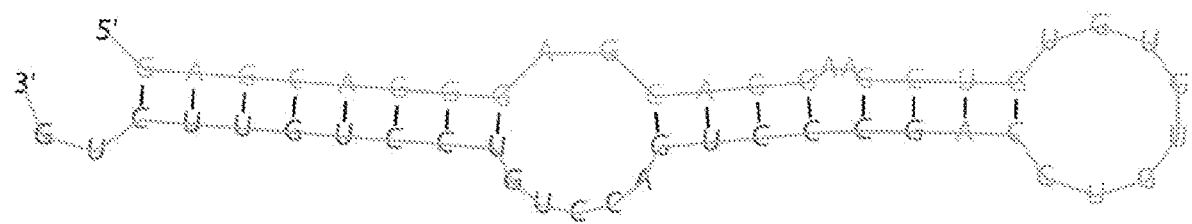
Figure 3D:
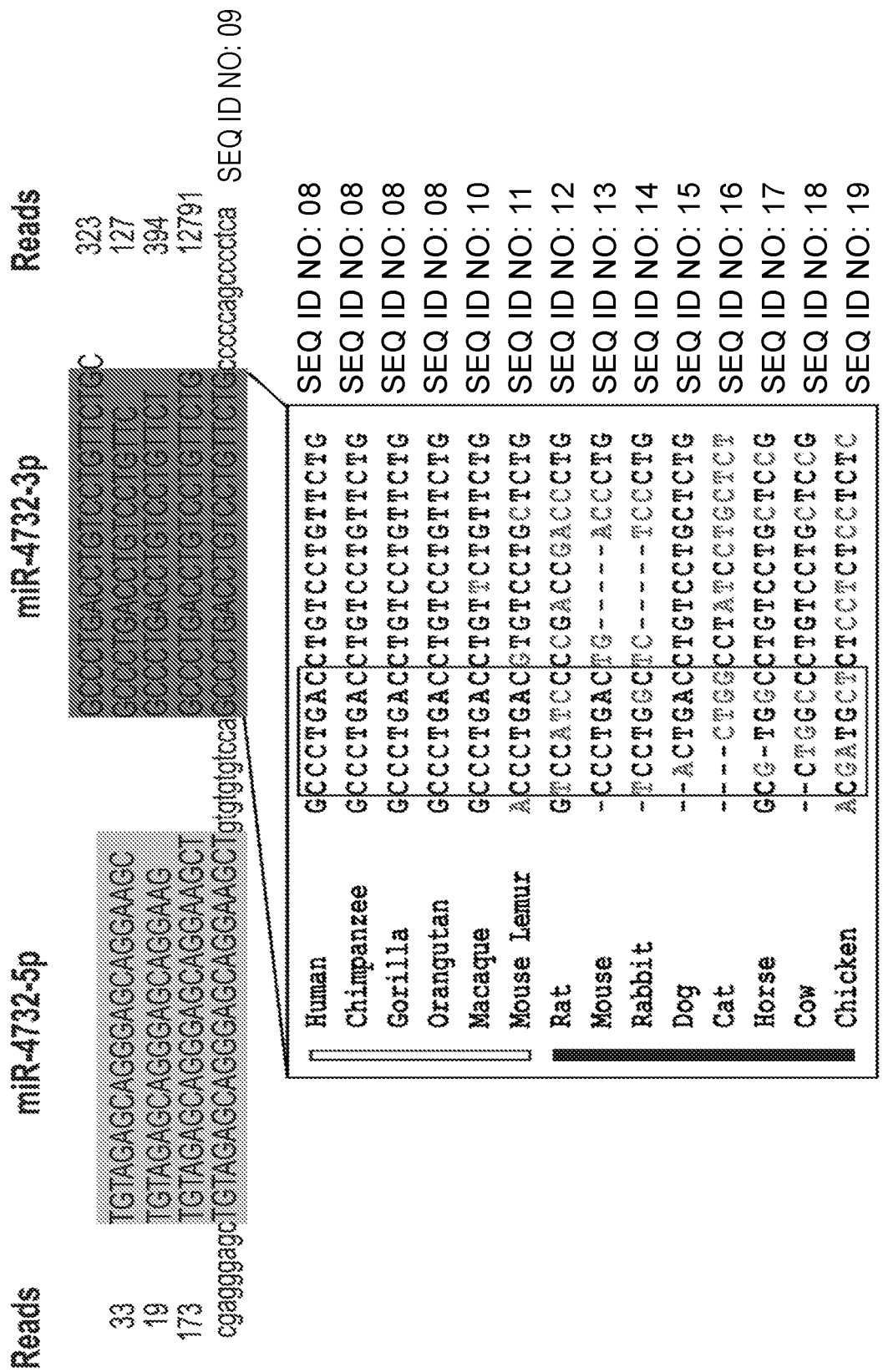

MirDeep maps miR-4732 to a predicted pre-microRNA canonical stem-loop folding structure with distinct 5p- and 3p-mature sequence reads (FIG. 3C), indicative of a bona fide microRNA. Interestingly, miR-4732-3p is primate-specific, with full seed sequence identical only among primates. Within non-primate species, it is poorly conserved, with both seed and non-seed mismatches (FIG. 3D). In contrast, miR-451a, miR-144-3p, and miR-144-5p are all highly conserved among primate and non-primate species. Together, the significant miRDeep score (Pottgiesser et al. (2009) *Vox sanguinis* 96:333-6, Kannan et al. (2010) *Transfusion* 50:1581-8), predicted pre-microRNA structure, and proximity to the miR-144/451 locus underscores the authenticity and potential functional relevance of miR-4732-3p.

Example 4: MiR-4732-3p Directly Regulates SMAD2 and SMAD4

Using the microRNA target prediction tool Targetscan (Lewis et al. (2005) *Cell* 120:15-20), 556 genes were predicted to be regulated by miR-4732-3p. A GATHER analysis was performed (Chang et al. (2006) *Bioinformatics* 22:2926-33) to identify the related predicted target pathways among the target genes. Significant enrichment in TGF-β signaling was identified, with literature networks and protein-binding networks for SMAD3 (Chang et al. (2006) *Bioinformatics* 22:2926-33). SMAD2 and SMAD4 are both predicted to be regulated by miR-4732-3p, with conserved seed sequence binding sites in most species. TGF-β family cytokines bind to associated membrane receptors, promoting receptor-mediated phosphorylation of SMAD2 and SMAD3 to associate with SMAD4 (He et al. (2006) *Cell* 125:929-41). This activated SMAD2/3 complex binds to competing effectors SMAD4 or TIFγ to fine-tune a balance between erythroid differentiation and proliferation (Nakao et al. (1997) *The EMBO Journal* 16:5353-62). TGF-β activates the expression of several SMAD4 target genes, including pai-1, p21, bim, and bax (Chen et al. (2007) *The Journal of Biological Chemistry* 282:9688-95), Dong et al. (2014) *Cellular Signaling* 26:1089-97), shown to reduce cell viability and proliferation. For example, PAI-1, Bim, and Bax act as activators of apoptosis and trigger cell death (Harada et al. (2003) *Reviews in Clinical and Experimental Hematology* 7:117-38, Balsara et al. (2008) *Thrombosis and Haemostasis* 100:1029-36). In addition, p21 is a potent cell cycle inhibitor that binds to and inhibits the activity of cyclin-CDK2, -CDK1, and -CDK4/6 complexes (Ferrandiz et al. (2012) *PloS One* 7:e37759). The induction of these genes by TGF-β is consistent with ability of TGF-β to inhibit proliferation and increase cell death during erythropoiesis (Zermati et al. (2000) *Experimental Hematology* 28:885-94). Inhibition of SMAD2 or SMAD4 results in increased erythroid cell proliferation (Dong et al. (2014) *Cellular Signaling* 26:1089-97, Randrianarison-Huetz et al. (2010) *Blood* 115: 2784-95, Choi et al. (2005) *Molecular and Cellular Biochemistry* 271:23-8, Dussiot et al. (2014) *Nature Medicine* 20:398-407, Suragani et al. (2014) *Nat Med.* 20:408-14), but their effects on differentiation are inconsistent. However, much remains unknown about the upstream signals that coordinate the regulation of these factors.

Figure 4B:
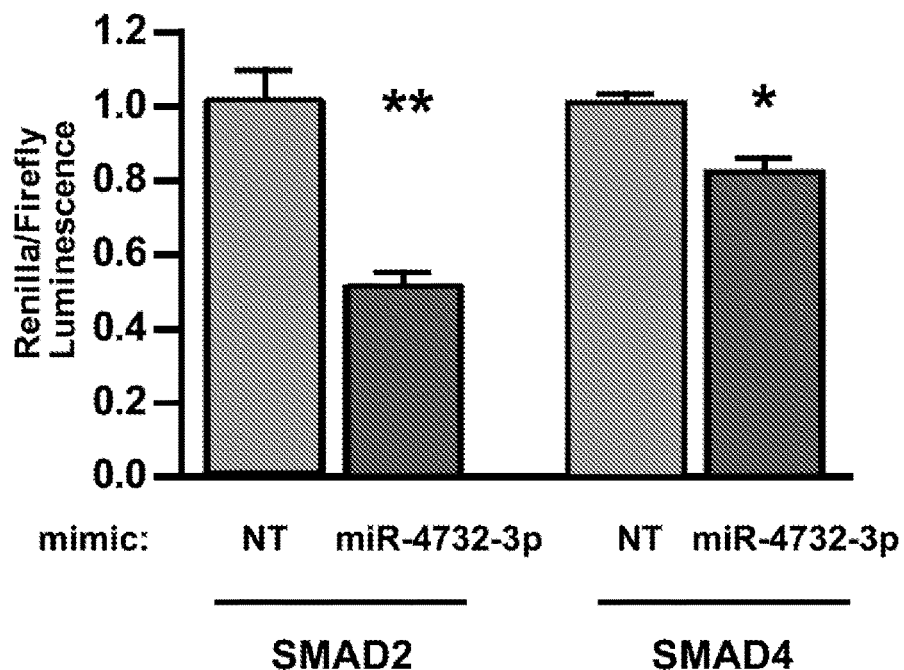
Figure 4C:
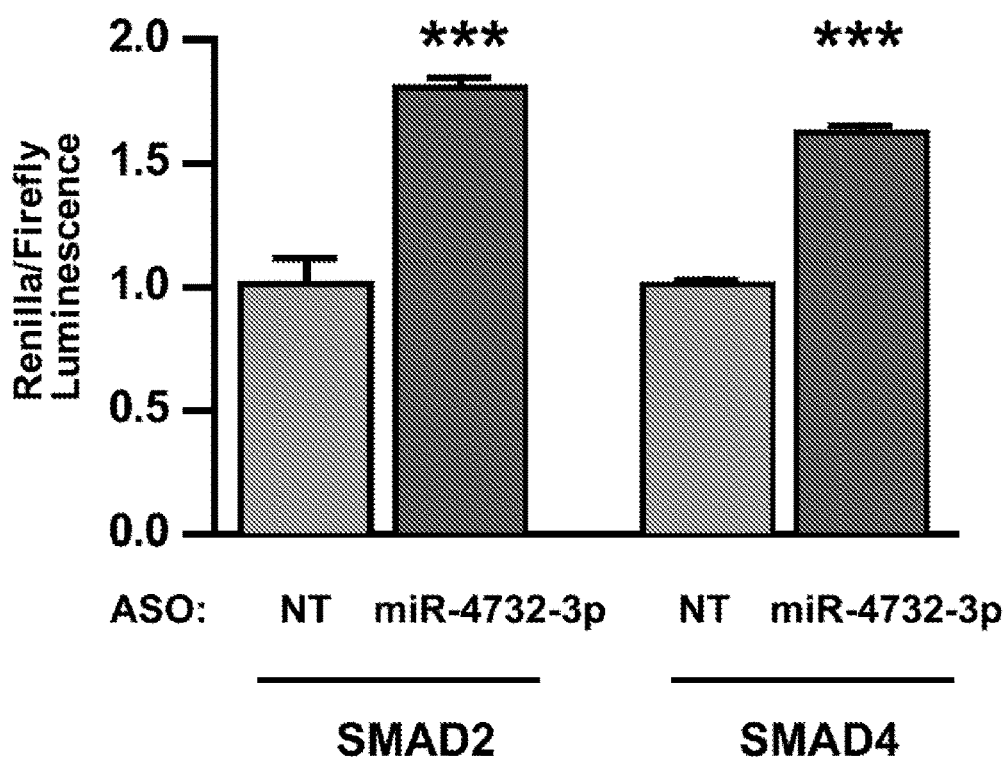
Figure 4D:
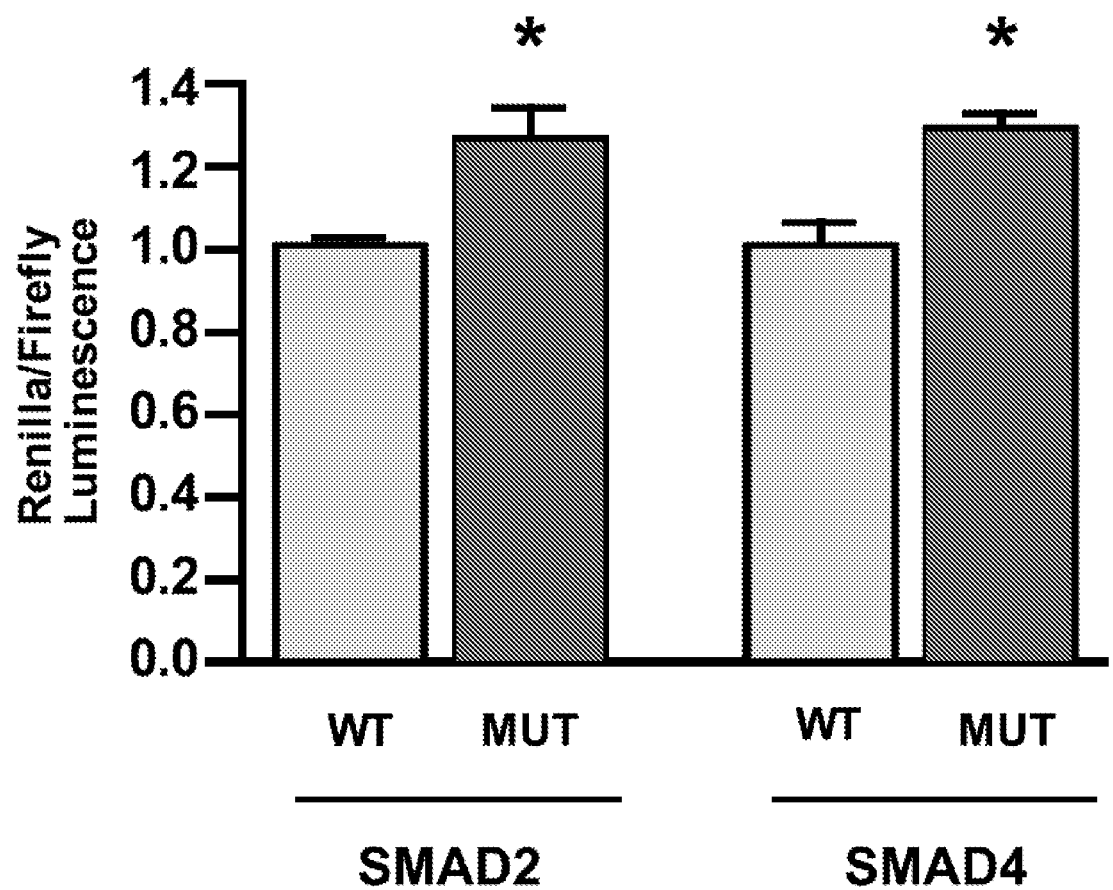

Based on these predictions and biological relevance, the potential of miR-4732-3p to regulate SMAD2 and SMAD4 was investigated (FIG. 4A). To test whether both of these predicted targets contain bona fide repressive elements, portions of 3'UTR of SMAD2 and SMAD4, including the predicted target sites, were cloned into a dual luciferase reporter. As shown, transfection with a miR-4732-3p mimic significantly repressed normalized *Renilla* 3' UTR reporter activities of both SMAD2 and SMAD4 in K562s, indicating the ability of miR-4732-3p to regulate SMAD2/4 (FIG. 4B). To determine whether endogenous miR-4732-3p repression would affect reporter expression, miR-4732-3p was inhibited with an antisense oligonucleotide (ASO) and observed increased relative *Renilla* reporter activities for both SMAD2 and SMAD4 (FIG. 4C). This regulation occurs through the predicted target miR-4732-3p binding sites, as mutation of the respective target sequences in the 3' UTR of SMAD2 and 4 abrogated the endogenous microRNA-mediated luciferase repression (FIG. 4D).

Figure 4E:
Figure 4E:
Figure 4E:
Figure 4F:
Figure 4F:
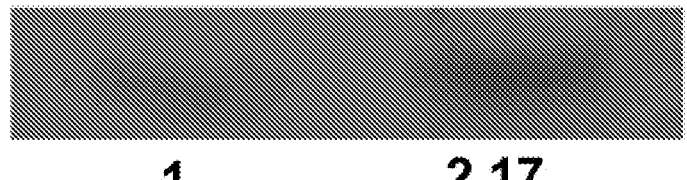
Figure 4F:
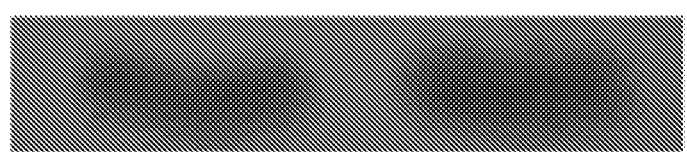

To understand the in vivo relevance of the regulatory relationship between miR-4732-3p and SMAD2/SMAD4, it was determined whether miR-4732-3p inhibits the protein levels of SMAD2 and SMAD4 (FIGS. 4E and 4F). Transfection of miR-4732-3p mimics in K562s reduced the protein levels of both SMAD2 and SMAD4 (FIG. 4E), whereas inhibition of miR-4732-3p increased the levels of SMAD2 and SMAD4 protein (FIG. 4F). Thus, miR-4732-3p inhibits the protein levels of both SMAD2 and SMAD4 through a canonical microRNA-mediated regulation of 3' UTRs.

Example 5: miR-4732-3p Regulates the TGF-β Signaling Cascade

Figure 5A:
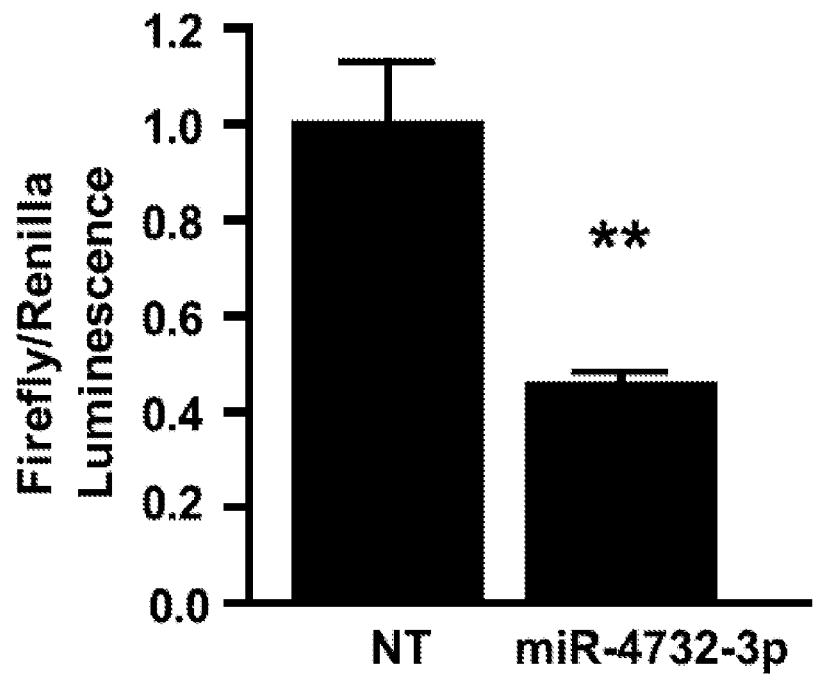
FIG. 5A-5D shows that MiR-4732-3p regulates TGF-β signaling and promotes erythroid cell proliferation.
Figure 5B:
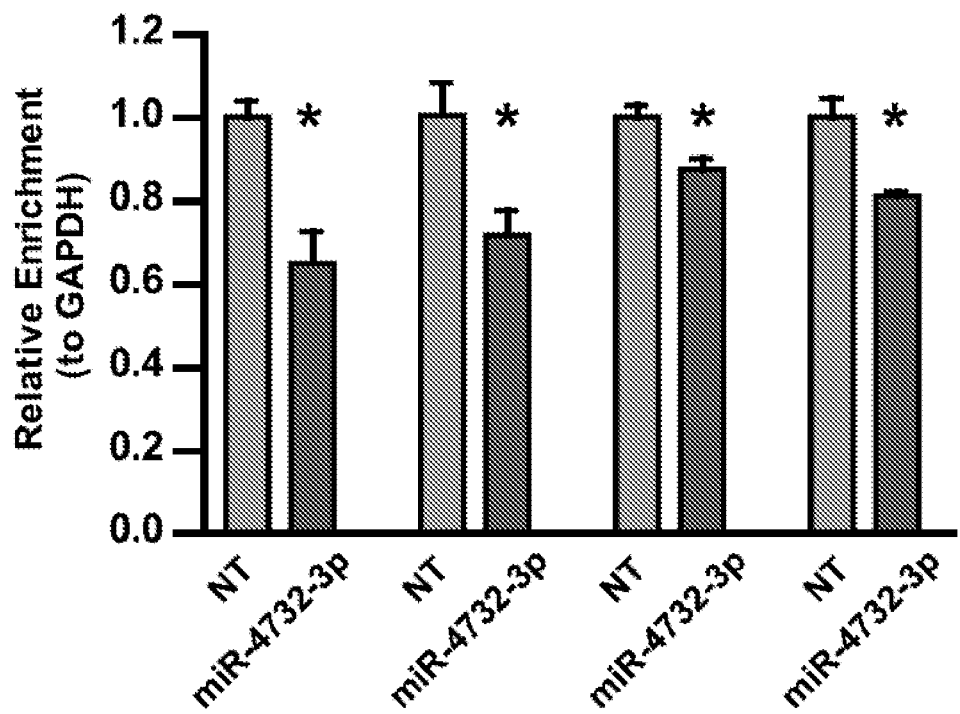

Next, whether miR-4732-3p-mediated downregulation of SMAD2 and SMAD4 would affect TGF-β signaling was assessed. TGF-β pathway activities were measured with a Firefly luciferase TGF-β reporter construct driven by the SMAD4-dependent CAGA element promoter (CAGA-luc) (Dennler et al. (1998) *The EMBO Journal* 17:3091-100). Overexpression of miR-4732-3p in K562s resulted in a significant reduction in relative reporter luciferase values (FIG. 5A), demonstrating that miR-4732-3p suppresses SMAD4-mediated transcription activities. Additionally, whether miR-4732-3p overexpression can affect the level of SMAD4-dependent target genes, such as pai-1, p21, bim, and bax (Chen et al. (2007) *The Journal of Biological Chemistry* 282:9688-95, Dong et al. (2014) *Cellular Signalling* 26:1089-97) was determined. Overexpression of miR-4732-3p significantly reduced the expression of all these SMAD4-regulated genes (FIG. 5B).

Figure 5C:
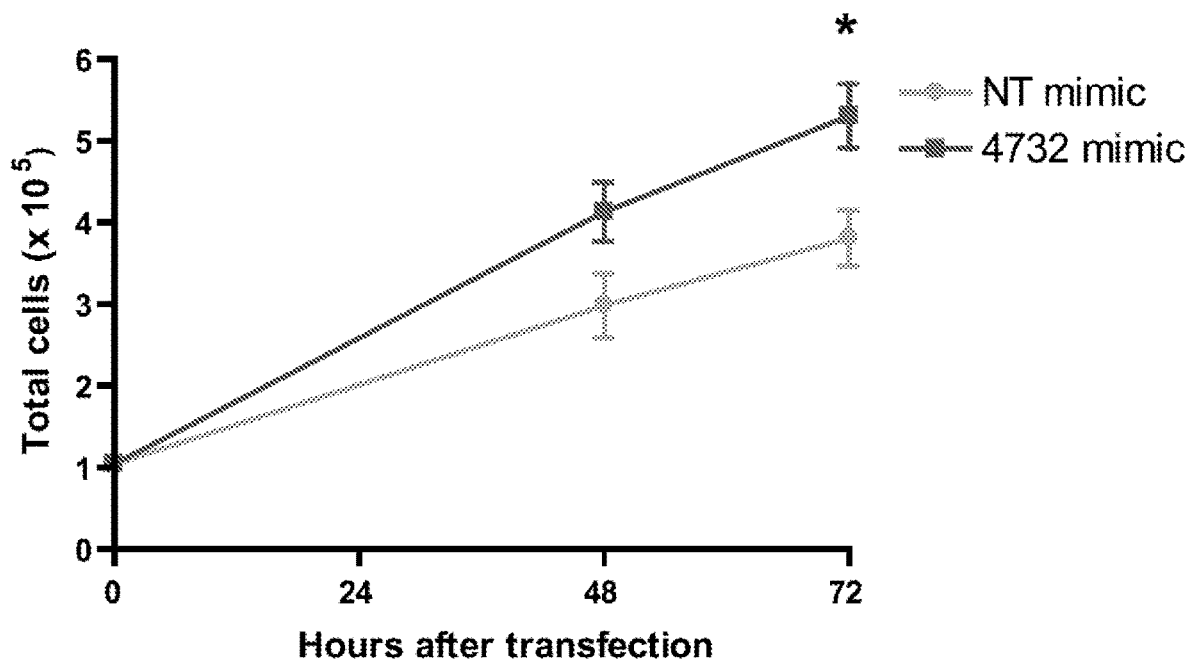
Figure 5D:
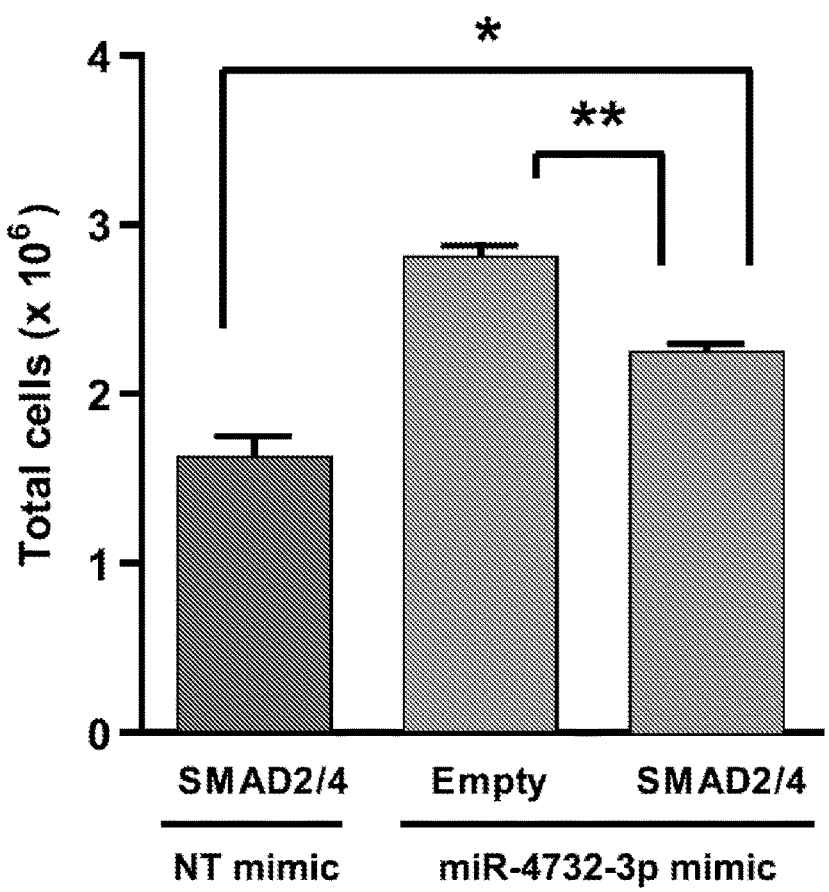

Given the ability to suppress TGF-β signaling activity, miR-4732-3p can promote proliferation by suppressing SMAD2 and SMAD4. Indeed, overexpression of miR-4732-3p in differentiating CD34+ erythroid progenitors resulted in a significant increase in total cell number (FIG. 5C). Furthermore, the miR-4732-3p-mediated increase in cell number was abolished by overexpression of SMAD2 and SMAD4 with cDNA constructs lacking miR-4732-3p-responsive 3'UTRs (FIG. 5D). These results indicated that miR-4732-3p increased erythroid cell number by repressing the levels of SMAD2/4. Together, these data demonstrated that miR-4732-3p modulates TGF-β signaling to promote erythroid cell survival and production during erythropoiesis.

Example 6: Identification and Validation of "Storage" RBC Gene Signatures

To define the transcriptomic changes during red cell storage, differential analysis of the microRNA expression of RBCs were compared during different time points during in vitro blood storage.

Figure 6:
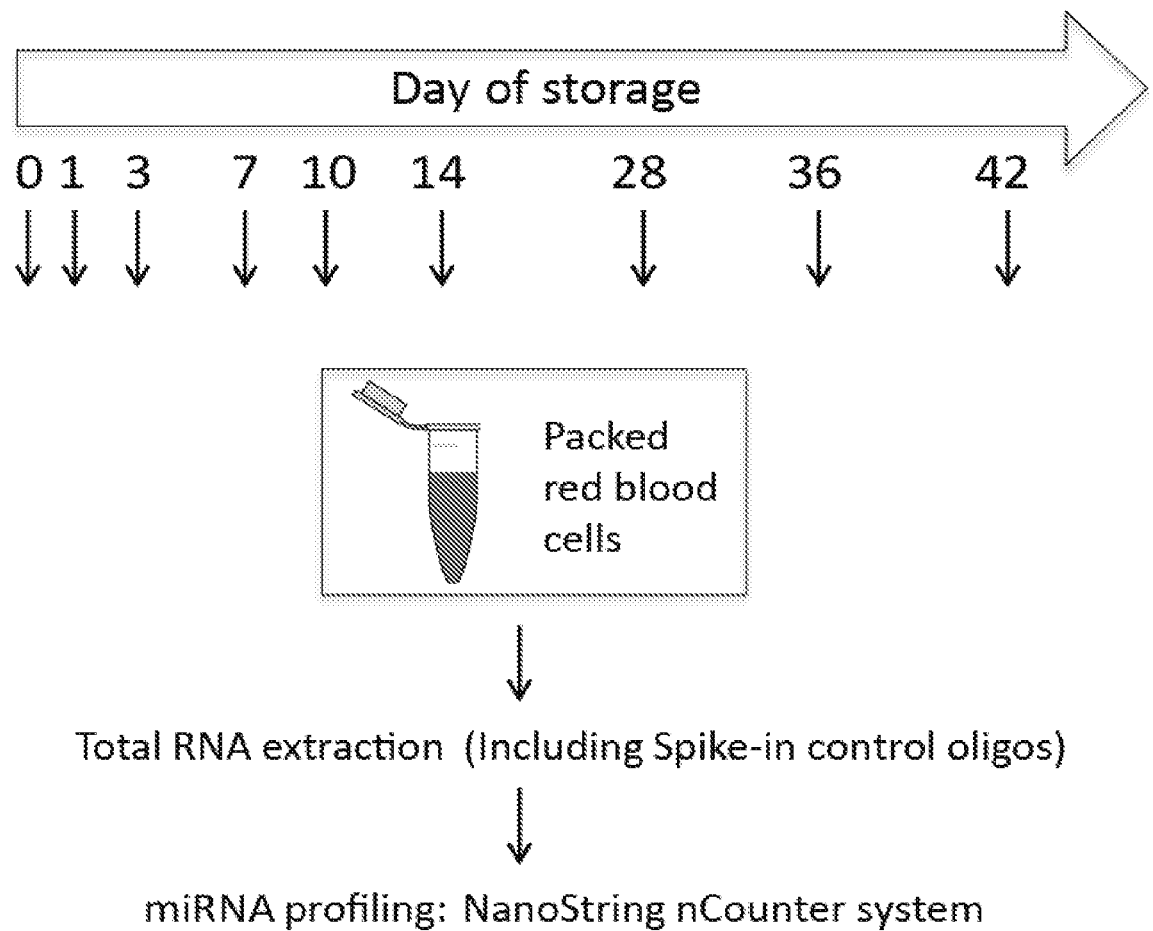
FIG. 6 is a schematic showing the experimental design of the experiments to profile the transcriptome changes of RBCs during indicated days of storage.

Profiling of RBC microRNA Changes During In Vitro Storage:

The microRNA expression of stored RBCs was compared during different time points during in vitro blood storage to identify the subset of microRNAs with significant changes, either common or unique for each individual, during blood storage. Whole blood of 250 ml (half units) were obtained by phlebotomy from 3 healthy adult volunteers using procedures of the American Red Cross, consistent with the Technical Manual of the AABB, and processed in conventional fashion including leukofiltration, centrifugation and stored using CPDA-1 at 4° C. in a monitored refrigerator. The RBCs from 5 ml aliquot of fresh blood was purified for RNA isolation. For the stored blood, 20 ml was removed at the following time points: day 1, day 3, day 7, day 14, day 21, and day 35 or day 42 (expiration). Removal of aliquots was accomplished anaerobically via a sterile-docking device fitted with a valve to ensure there is no re-entry of air, or other contamination, into the RBC unit. The RNA isolated from these aliquots were analyzed by nCounter miRNA kits to profile the microRNA expression. (FIG. 6) Remaining RNA samples were stored for additional backup and validation purpose. The microRNA expression was normalized by doping non-human microRNAs as well as other endogenous microRNAs found to be stable during in vitro storage. Unsupervised hierarchical clustering, k-nearest-neighbor classification and class prediction methods were used to determine the set of microRNAs able to classify the samples into fresh vs. stored and their classification accuracy.

The mirVana kit was used to purify all the RBC RNA aliquots from the collected samples. First, there are significant variations in the amount of RNA per cells from different donors that persist up to 42 days of storage. Given the absence of novel RNA synthesis, the RBC RNA should be expected to become degraded with time during the 42 days of storage. However, while there were varying amount of RNA levels at different time points, the RNA contents did not decrease with time. Instead, the RNA contents were mostly stable in all samples.

The purified RNA samples were then submitted to Nanostring headquarters in Seattle and analyzed by Nanostring nCounter miRNA kits to profile the microRNA expression. For the profiling of RBC microRNAs, the nCounter microRNA Expression Assay (Nanostring, Seattle, Wash., United States) was used for multiplexed, direct digital detection and counting of microRNAs in a single reaction without amplification. The assay includes >800 mature and pre-microRNAs found in miRBase v18 using Mega BLAST as well as 17 control housekeeping microRNAs for normalization. MicroRNAs from other species were doped in as controls, including (cel-miR-254, osa-miR-414, osa-miR-442). The differentially expressed transcripts utilized for classification will be further validated Three doping microRNAs were chosen from other species (cel-miR-254 (*C. elegans*), osa-miR-414 (*Oryza sativa*), osa-miR-442 (*Oryza sativa*)) to monitor the technical performance and allow for normalization. The microRNA expression was normalized by several doped-in endogenous controls in the nCounter kit, as well as several endogenous microRNAs found to be stable during storage. When the normalized microRNAs were analyzed from all samples, it was found that the Emory samples (RNA isolated at Emory at time zero) were distinct from the Duke samples (all samples from day 1-42 with RNA isolated at Duke). While there were many potential biological and technical reasons for these differences, the time zero point was removed from further analysis.

Data Analysis and Signature Development:

Data from the nCounter microRNA Expression Assay were normalized using the manufacturers' pipeline. The transcriptome changes were then identified by a process called zero-transformation that compared the abundance of all microRNAs against the abundance of the same microRNAs in the day 1 sample of that donor. The induced and repressed microRNAs were further validated by using TaqMan® real-time RT-PCR for microRNA and other transcripts normalized by the doped foreign microRNAs and several endogenous microRNAs and relative quantification by the 2−ΔΔCt method.

Figure 7A:
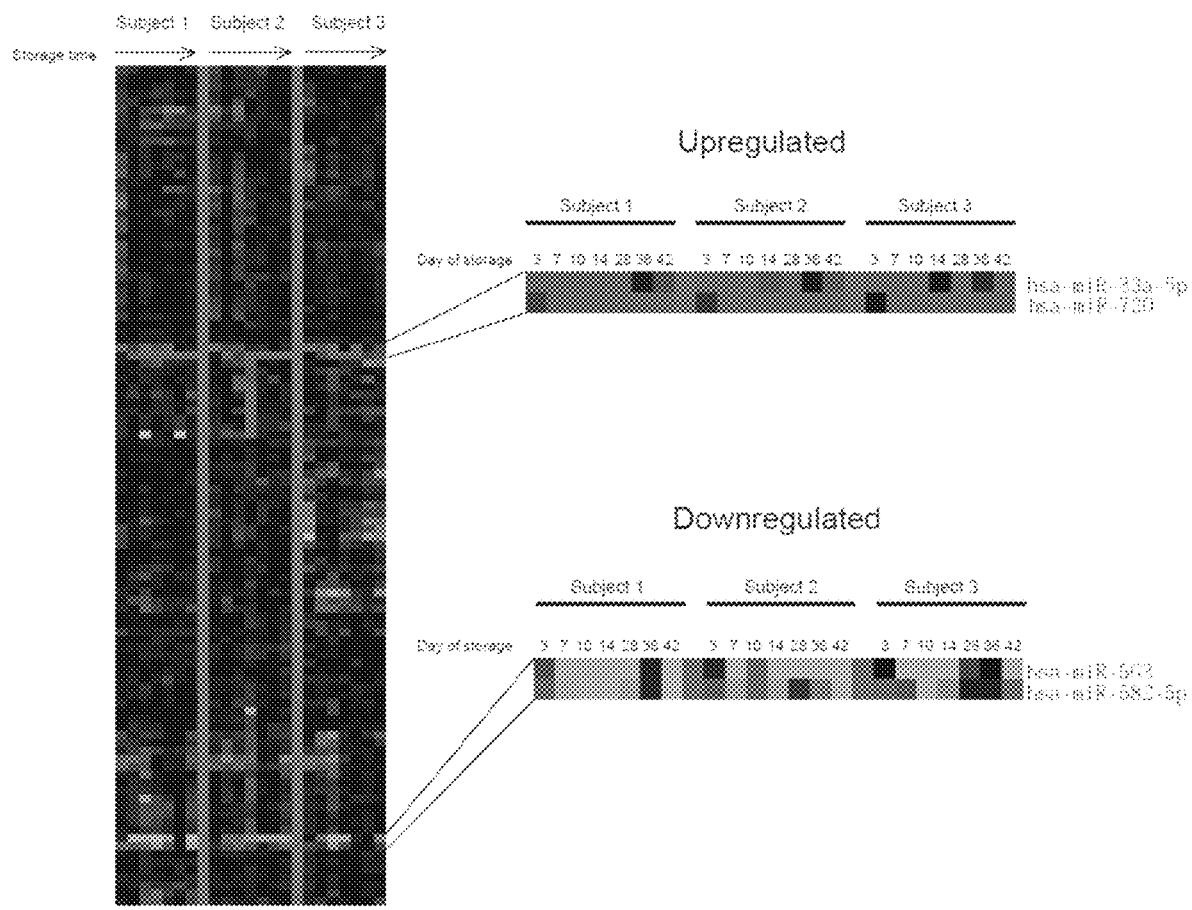
FIG. 7A: Heatmap of all microRNAs during in vitro storage. The increased and repressed microRNAs were shown in red and green. The two induced and two repressed microRNAs were expanded and indicated.

Zero-transformation was performed to determine the changes of all microRNAs against the day 1 sample for each individual donor (Chen et al. (2008) *PLoS One* 3:e2360, Chen et al. (2008) *PLoS Genet.* 4:e1000293, Chen et al. (2010) *PLoS Genet.* 6). These changes were then grouped by their similarity of transcriptional changes as shown in the overall heatmap (FIG. 7A). From these analyses, most microRNAs do not show consistent changes (shown in FIG. 7A, black dots in the heatmap and FIG. 7B by the overlapping black lines). This is consistent with the persistent abundance of overall RNA in all RBC samples analyzed.

Figure 7B:
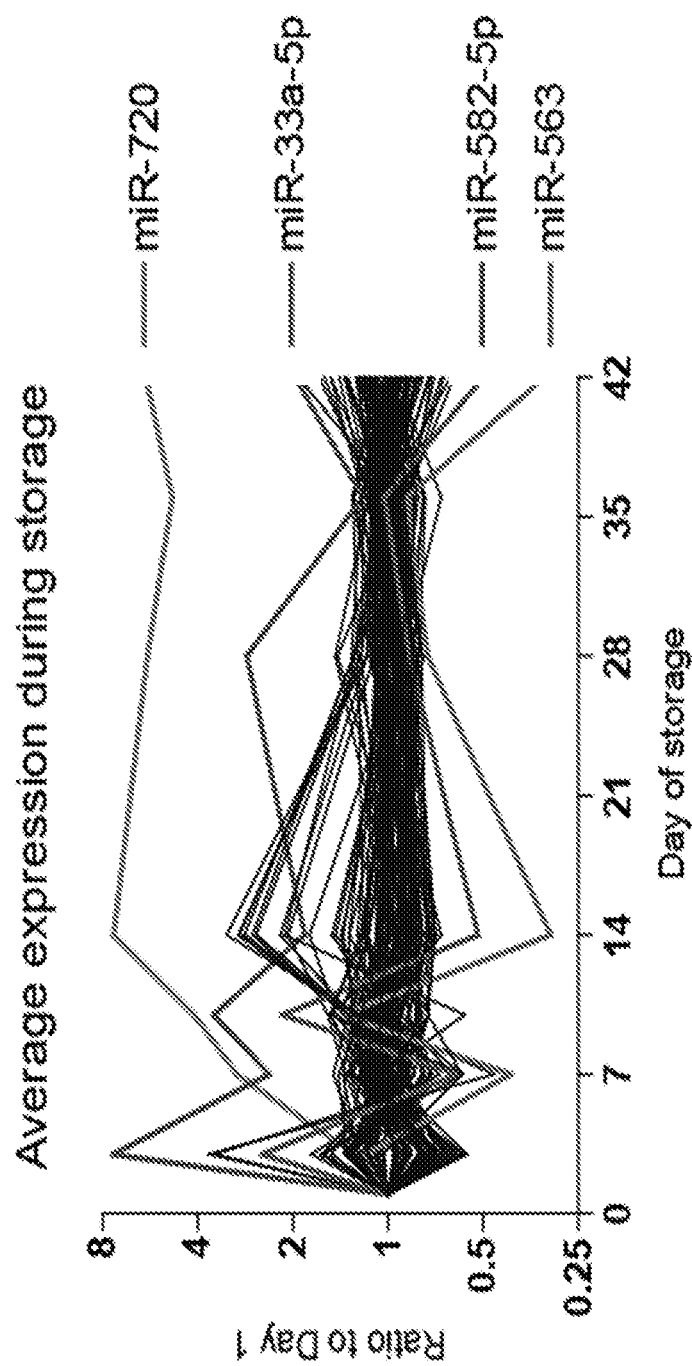
FIG. 7B: shows the folds of changes of four microRNAs with consistent changes during storage, including two increased (miR-720, miR-33a-5p) and two reduced microRNAs (miR-582-5p, miR563) from day 1 for that donor (as baseline: 1) at indicated days of RBC storage. MicroRNA amounts were analyzed from stored RBCs from three different donors. Fold change for individual donor was compared to baseline amounts of that donor.

However, two induced and two repressed microRNAs were identified whose changes were consistent in all three samples and almost all time points. The increased microRNAs include miR-720 (SEQ ID NO: 31) and miR-33a-5p (SEQ ID NO: 32). The repressed two microRNAs were miR-563 (SEQ ID NO: 33) and miR-582-5p (SEQ ID NO: 34) (FIGS. 7A and 7B). The ratio between induced and repressed microRNAs can lead to even bigger changes to improve the specificity and sensitivity of detection. In addition, several microRNAs were identified whose levels were consistent all across time points and can serve as endogenous controls to avoid the use of doping control in the experimental setup.

These results identified at least two induced (miR-720 and miR-33a-5p) and two repressed (miR-563 and miR-582-5p) microRNAs during blood storage. The changes of these microRNAs are consistent in all tested samples and likely to comprise the storage signature that can be used to detect ABT.

Among all the consistently altered microRNAs, further studies were focused on miR-720. MiR-720 has been reported to have prognostic values as a diagnostic biomarker, and a functional role in suppressing tumor growth and invasion as well as T lymphocytes (Hara et al. (2013) *PLoS One* 8:e83545, Shinozuka et al. (2013) *Biochem Biophys Res. Commun.* 430:101-6, Li et al. (2014) *Carcinogenesis* 35:469-78, Tang et al. (2014) *Zhonghua Xue Ye Xue Za Zhi* 35:1009-12, Nonaka et al. (2015) *Int. J. Oncol.* 47:1097-102, Tang et al. (2015) *Cell Biosci.* 5:56, Wang et al. (2015) *Tumour Biol.* 36:719-27, Wang et al. (2015) *Sci. Rep.* 5:12159). However, recent studies have suggested the miR-720 is a fragment of threonine tRNA mimic. In fact, miR-720 has been removed from the most recent version of miRBase. However, this fragment is still referred to as miR-720 in the following discussion.

Figure 8A:
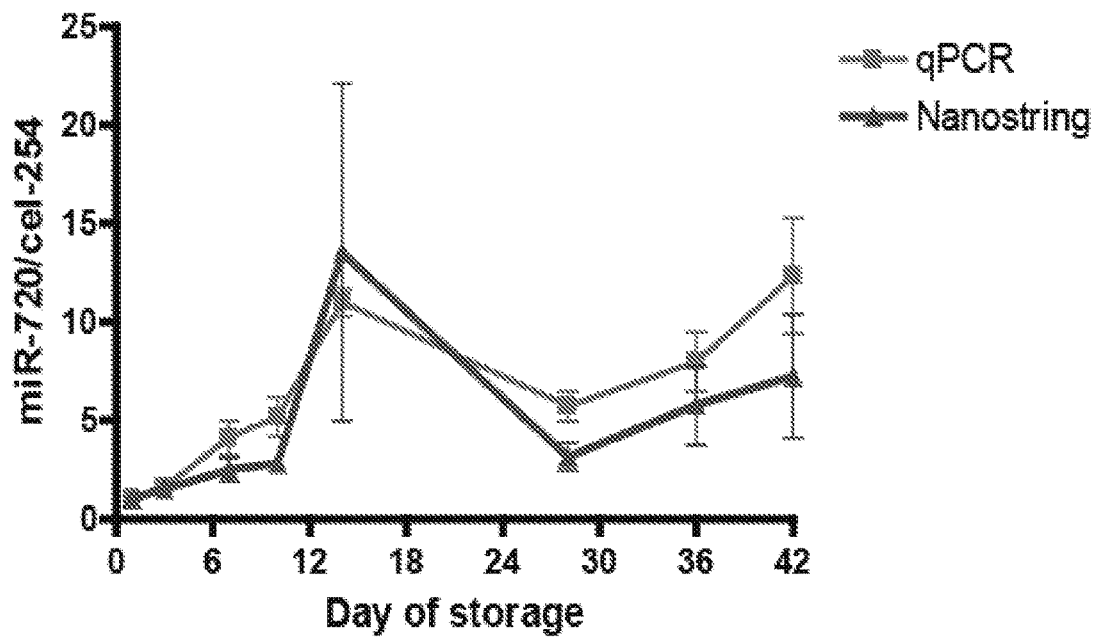
FIG. 8A-8C are graphs showing the RT-PCR validation of increased miR-720 when normalized against the doped foreign microRNAs, cel-254 (FIG. 8A), osa-414 (FIG. 8B), and osa-442 (FIG. 8C), which have been added into the storage samples to serve as technical controls. MicroRNA amounts were analyzed from stored RBCs from three different donors. Fold change for individual donor was compared to baseline amounts of that donor.
Figure 8B:
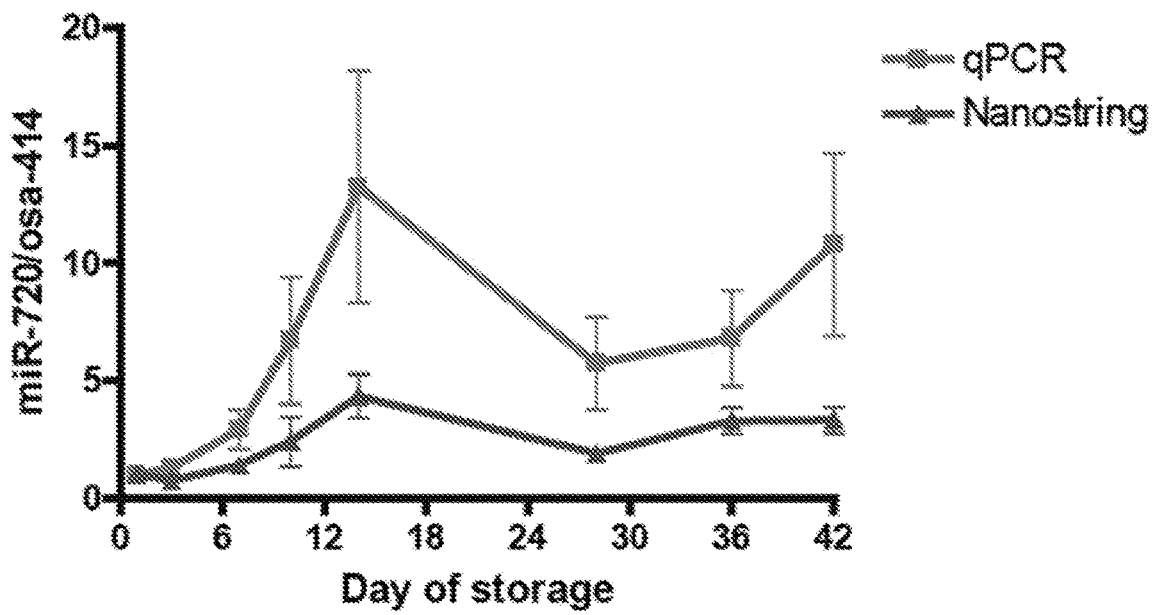
Figure 8C:
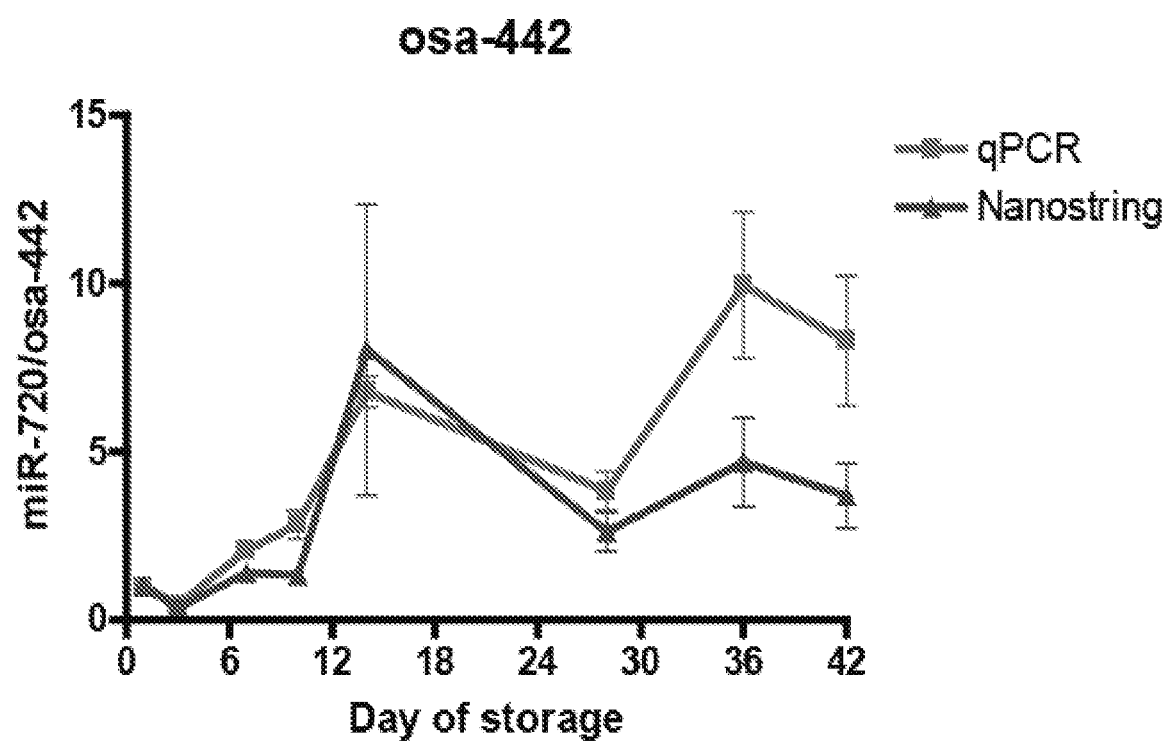

The increase of miR-720 was further validated by different methods to assess the reproducibility and robustness of miR-720 induction as a potential "storage gene signature." First, a custom-made assay for miR-720 (ABI) was used to determine whether the similar induction of miR-720 during in vitro storage would be observed by two different means of normalization. First, three doped foreign microRNAs (cel-miR-254, osa-miR-414, osa-miR-442) were used in the stored samples at different time points. As shown in FIG. 8, a significant (10-15 fold) increase in miR-720 was observed when the samples were normalized by RT-PCR with both miR-720 and doped foreign microRNAs (FIGS. 8A-8C). The doping foreign microRNAs are useful to provide a technical control.

Figure 9A:
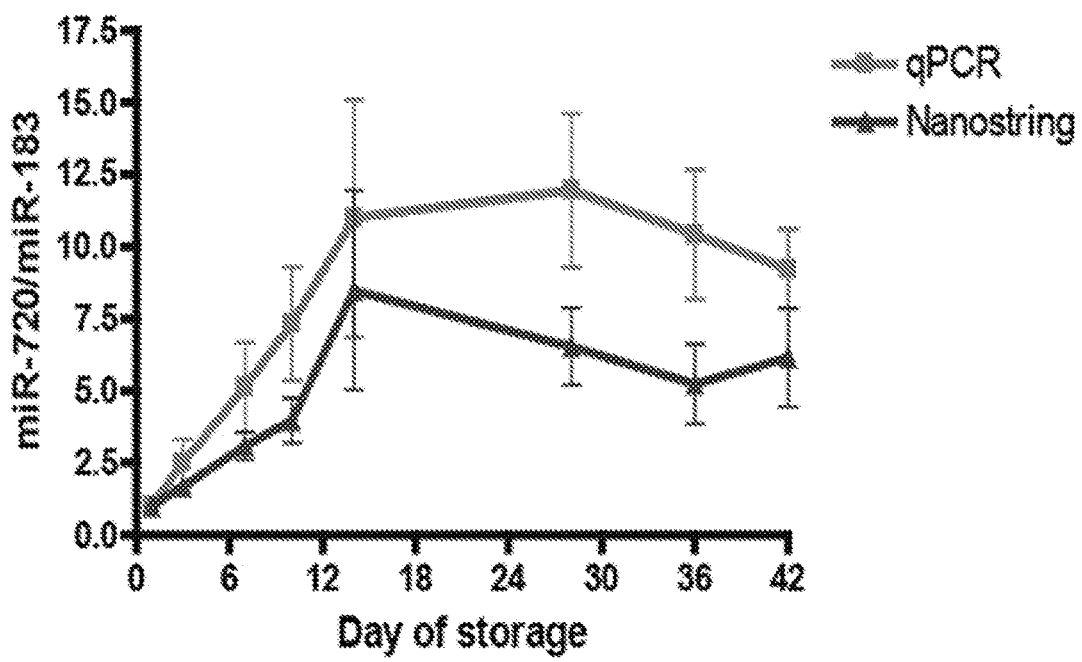
FIG. 9A-9C are graphs showing the RT-PCR validation of increased miR-720 when normalized against three endogenous microRNAs, miR-183 (FIG. 9A), let-7g (FIG. 9B), and miR-222 (FIG. 9C), which have been shown to be stable during in vitro storage. MicroRNA amounts were analyzed from stored RBCs from three different donors. Fold change for individual donor was compared to baseline amounts of that donor.
Figure 9B:
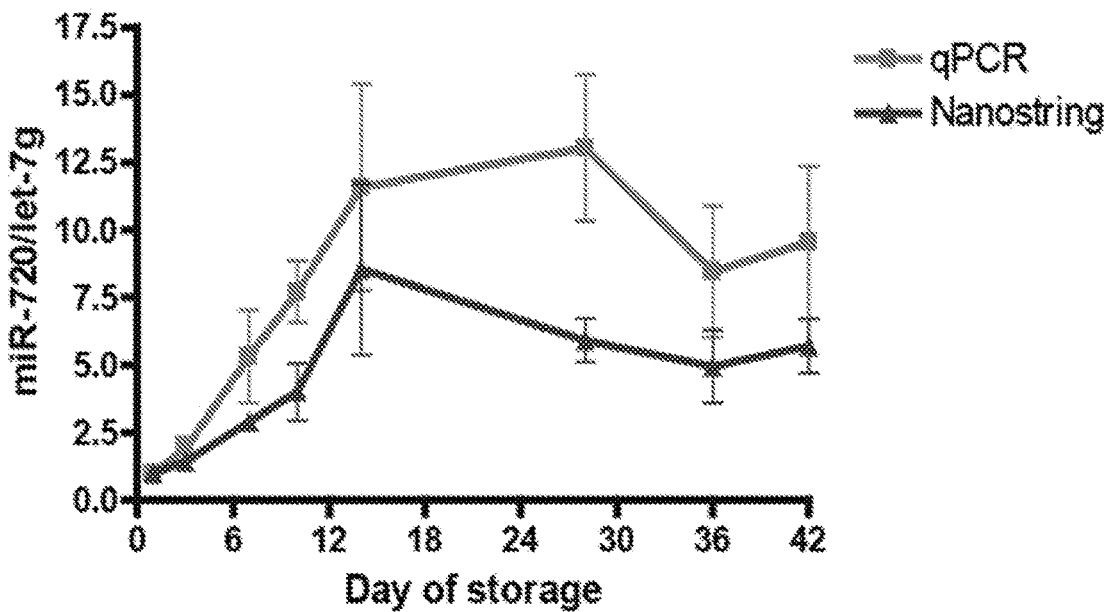
Figure 9C:
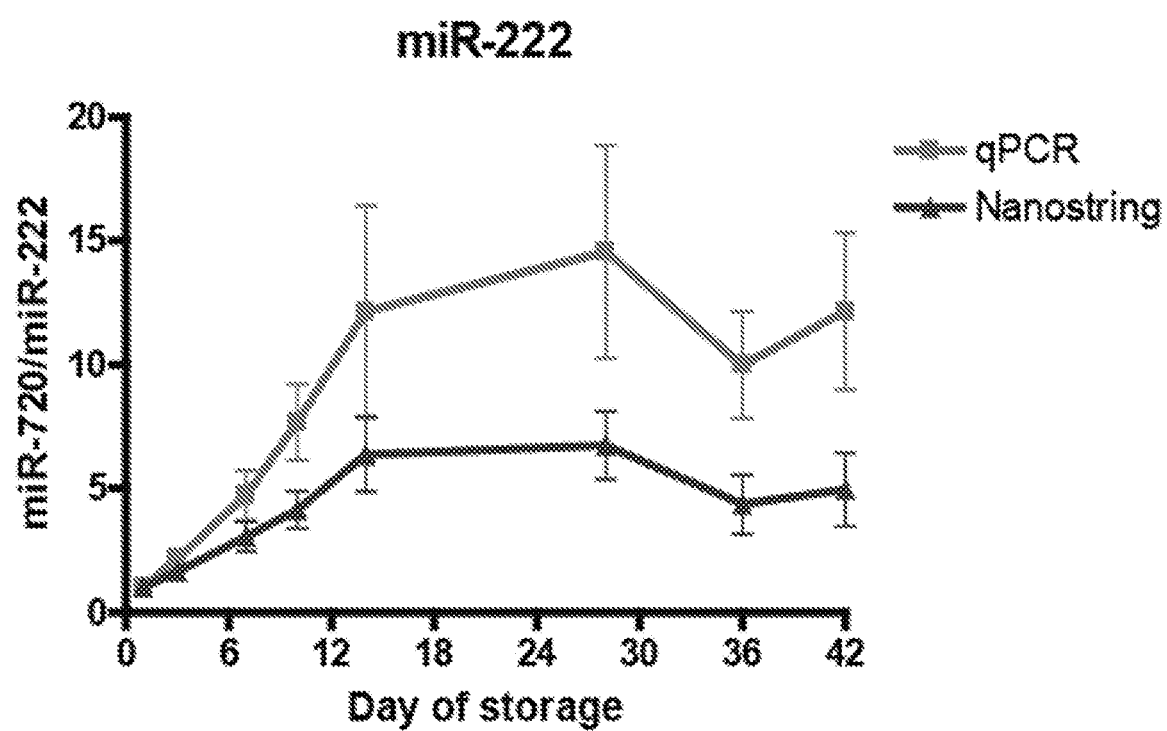

To test for ABT when normalized against endogenous RNAs, the heatmap was used to identify endogenous microRNAs whose levels showed little variations in different time points (FIG. 7A). Based on these analyses, miR-183, let-7g and miR-222 were found to be promising candidates for endogenous control for microRNA quantitation. These microRNAs are highly abundant in red blood cells and show little variations during in vitro storage. The miR-720 induction results when normalized against miR-183, miR-222 and let-7g were compared. As shown in FIGS. 9A-9C, all three endogenous controls showed the miR-720 induction that increased from day 1 to day 14. After day 14, miR-720 remained elevated throughput the 42 days of storage periods. Therefore, the miR-720 induction during in vitro storage is a robust and reliable signature for in vitro storage that can be reliably detected using RT-PCR.

Figure 10A:
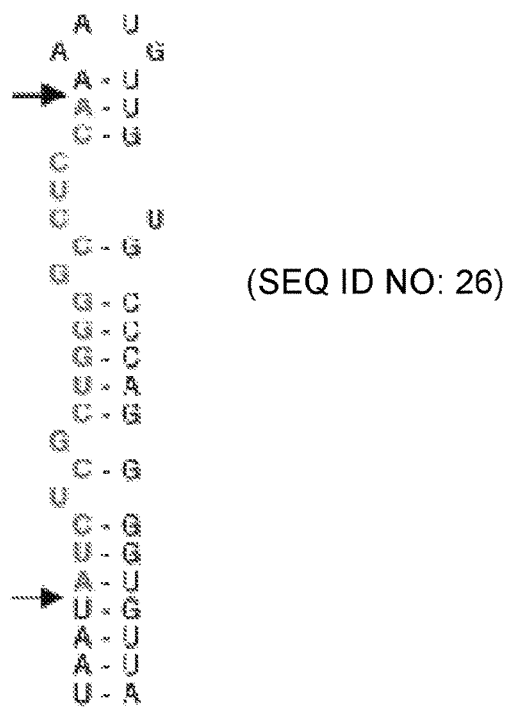
FIG. 10A-10B shows the RT-PCR validation of miR-720 and different fragments of tRNAs generated during in vitro storage.
Figure 10A:
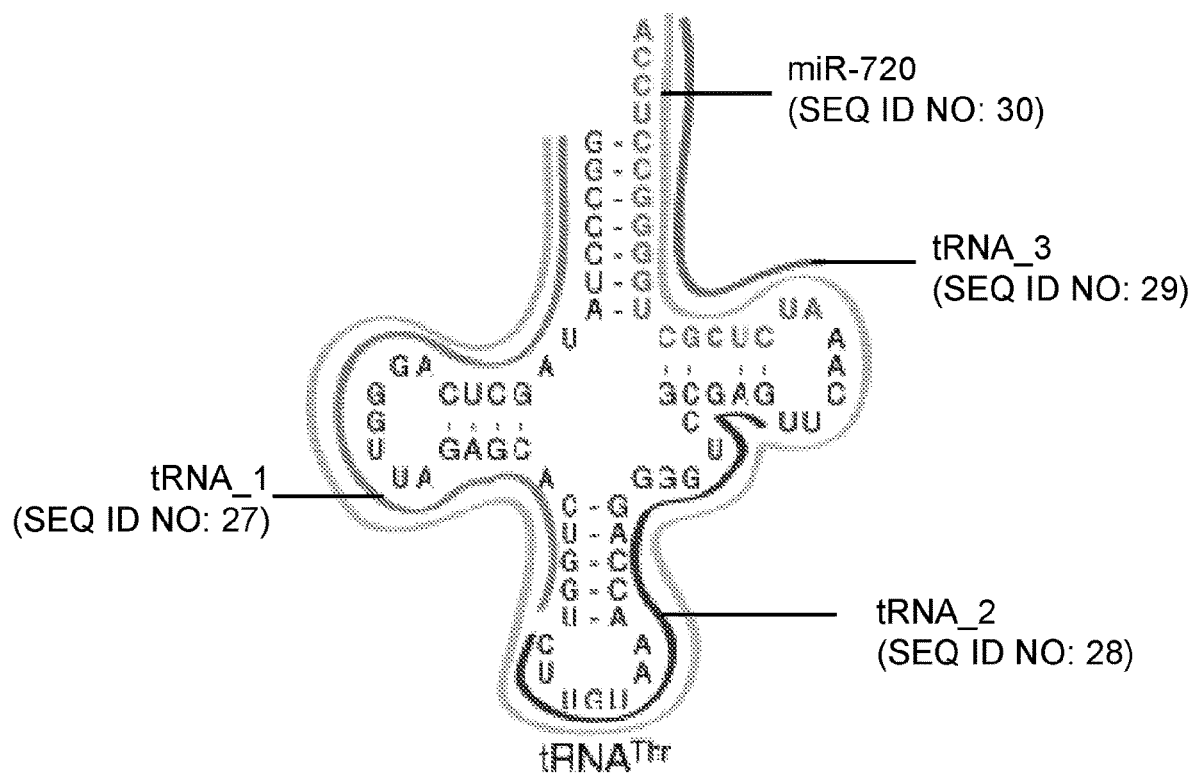
Figure 10B:
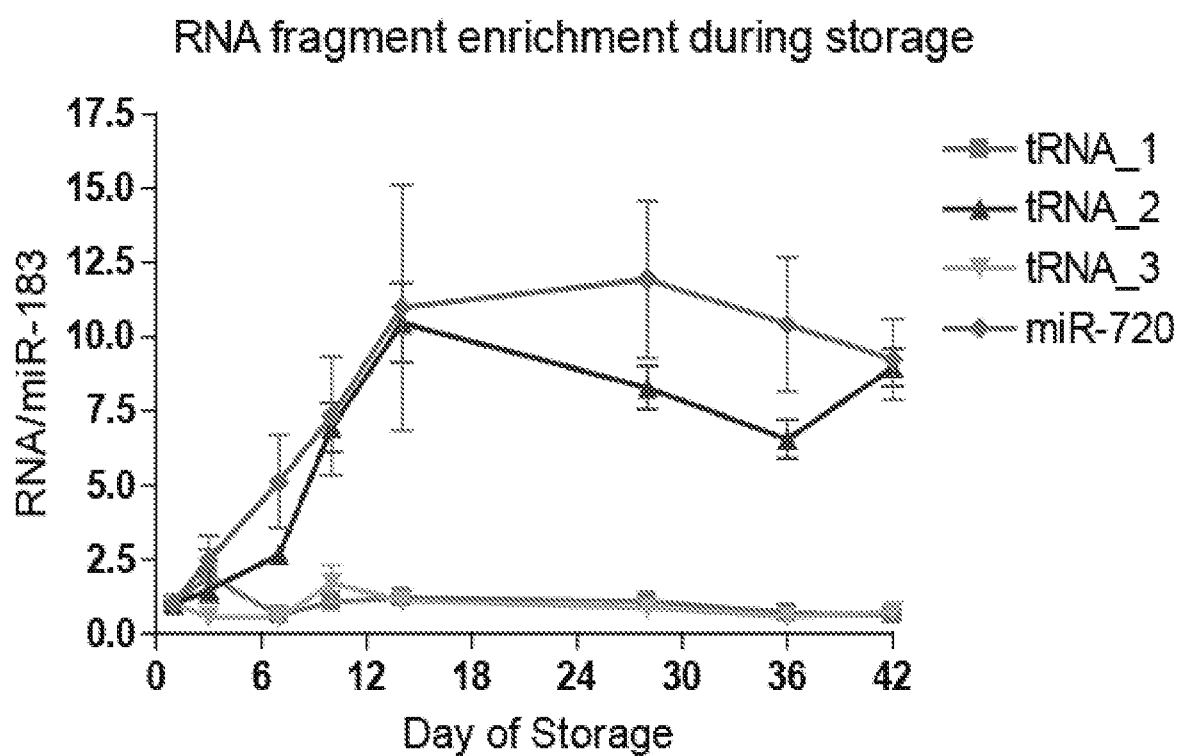
Figure 11:
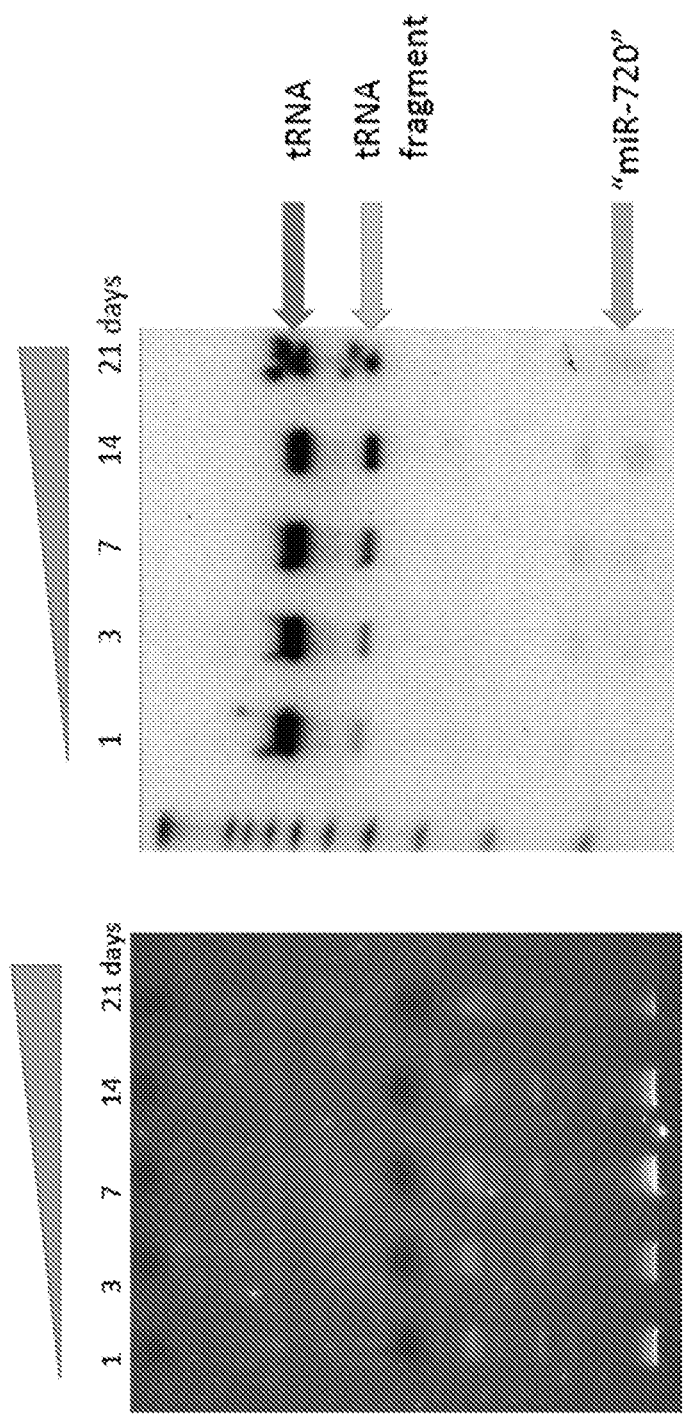
FIG. 11 shows gel electrophoresis images showing the increased miR-720 and reduced tRNAs during in vitro storage at indicated days.

Further analyses led to identification of other RNA fragments that change in abundance during storage. These fragments derive from the same noncoding RNA sequence mapping to the human genome. To test whether tRNA fragments of threonine are also elevated, custom-made primers were designed to detect various tRNA fragments (FIG. 10A). In addition to miR-720, one tRNA fragment was identified from threonine tRNA that was also significantly induced during storage (FIG. 10B). In addition, the RNA was separated from RBC stored at different time points on PAGE gel and transferred to a Nylon membrane. The Northern was further probed with LNA probe that recognized the miR-720 (FIG. 11). During the storage, it was found that the signal (17 bp) corresponds to miR-720 increased dramatically. Additional band of 55 bp also showed a corresponding increased during storage. Furthermore, a corresponding reduction in the tRNA signal of ~73 bp was observed (FIG. 11). Together, these results strongly support the concept that stored red cells have an exaggerated processing of tRNAs that lead to increase level of miR-720 and other tRNA fragments with a corresponding reduced level of the full length unprocessed tRNA.

A recent study also examined the changes in RBC microRNA composition during ex vivo storage (Sarachana et al. (2015) *Transfusion* 55:2672-83). While the paper claimed the identification of some changes associated with storage lesions, all the evaluated showed minimal changes. This particular study used Affymetrix microRNA arrays to determine the microRNA expression. This array platform does not have miR-720 on the array. Therefore, they did not find robust signatures of in vitro storage. In contrast, a 10-12 fold increase in miR-720 levels was observed in the studies described herein. Since miR-720 is a tRNA mimic fragment, other tRNA and tRNA mimic fragments, not considered as microRNAs, are also elevated. These possibilities suggest that the increased tRNA fragmentations, including miR-720, represent a multi-gene signature of blood storage.

Therefore, the discovery of a dramatic increase in the tRNA fragments during the routinely used storage conditions can be used to monitor storage of RBCs, and be used a method of quality control during storage. These tRNA fragments are reported to have significant biological activities and contribute to a "storage lesion" in red cells which have been stored for extended periods of time. Furthermore, angiogenin inhibitors provide a valuable role in blocking tRNA fragmentation, which inhibits formation of the RBC storage lesions. Additionally, while these experiments have supported the concepts of the miR-720 elevation as robust signature of in vitro storage, it is important to determine its ability to detect ABT in volunteers who received different amount of in vitro stored blood. These tRNA fragments provide sensitivity and specificity of these storage-signatures to detect ABT and doping of different amounts of blood.

Example 7: RNA-Seq Analysis to Identify Storage-Specific Transcripts

Figure 12A:
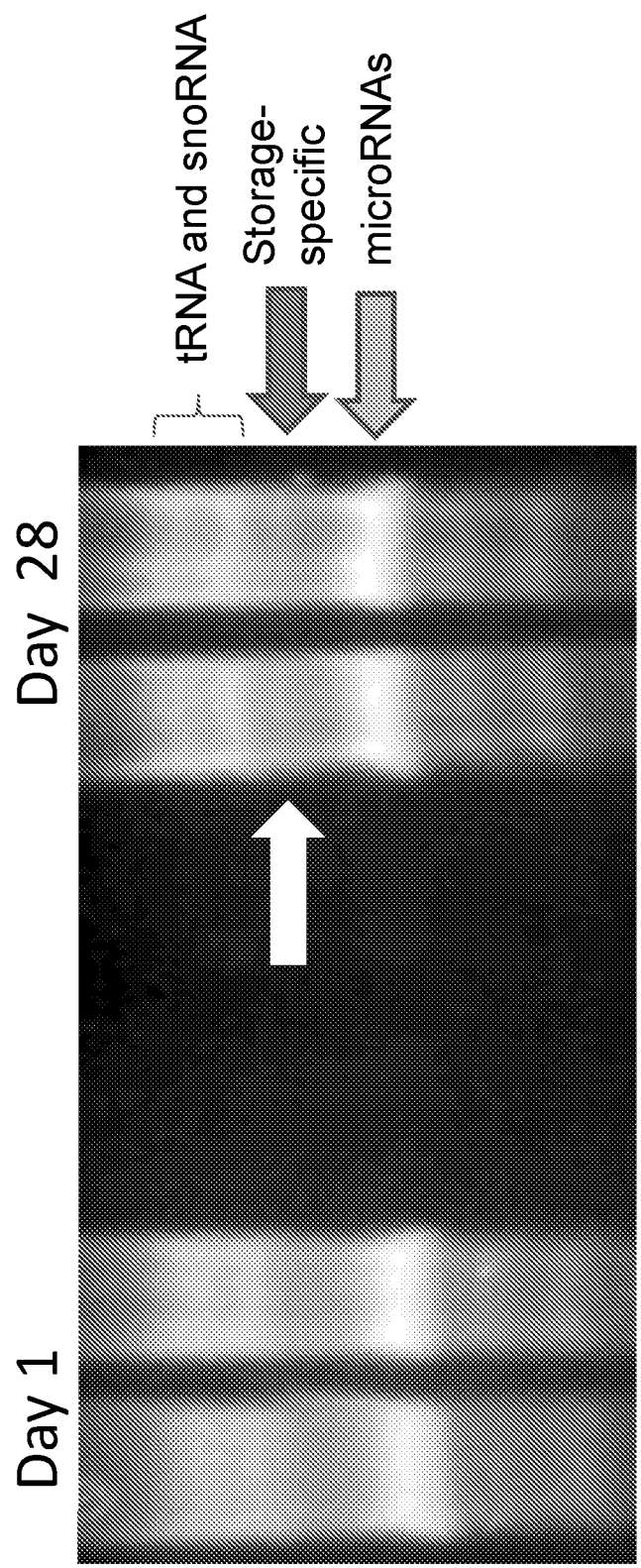
FIGS. 12A and 12B shows the generation of small RNA-Seq library for the fresh (day 1) and stored (day 28). With the indicated RNA species as well as storage-specific bands indicated by white arrow.
Figure 12B:
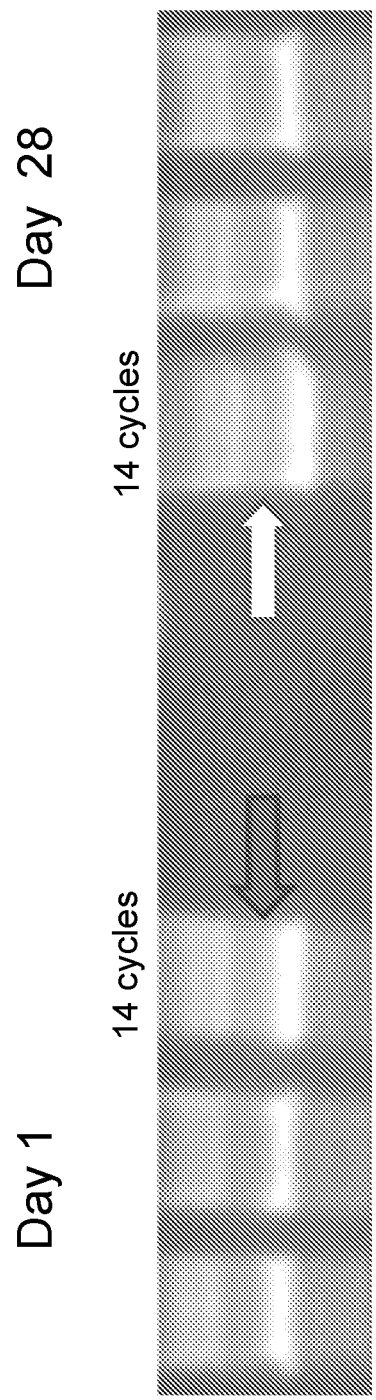
Figure 13:
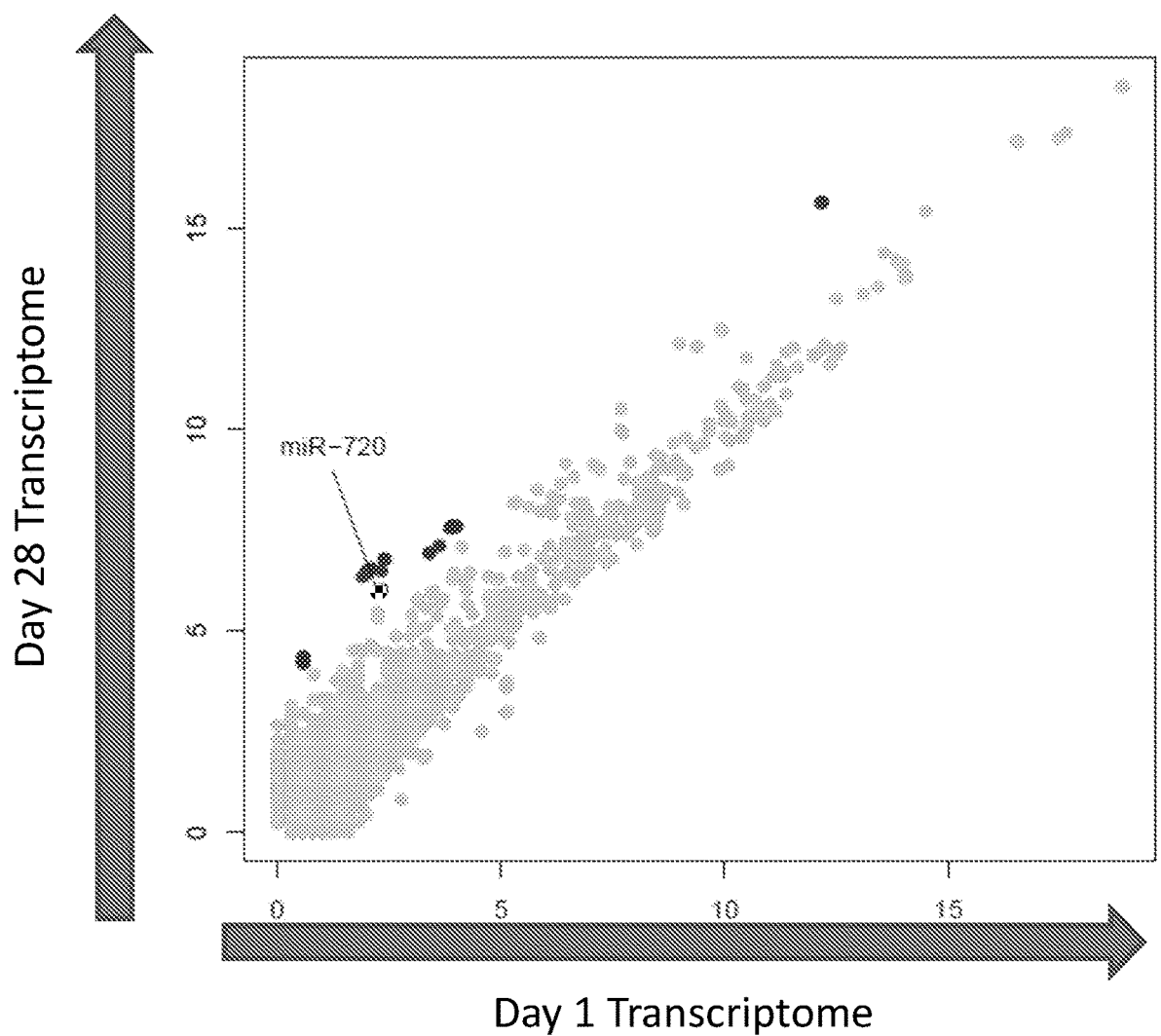
FIG. 13 shows the scatter plots of the RNA expression in the fresh (day 1) transcriptome (X-axis) and the stored (day 28) transcriptome (Y-axis) RBC. miR-720 (checkered dot) and 40 other storage-specific (>10 fold) transcripts (dark grey dots).

Illumina high-throughput RNA-sequencing was used to characterize small RNA populations in mature normal RBCs and identified hundreds of known microRNAs, 27 novel microRNAs, and other RNA species including mRNAs and tRNAs (Doss et al. (2015) *BMC Genomic* 16:952). Thus, while the previous analysis of stored RBC microRNA revealed a dramatic induction of mIR-720 during storage, RNA-Seq was also used to determine the global expression of transcripts during storage. Unexpectedly, during the RNA-Seq library preparation, two independent RNA-Seq libraries from the stored RBCs were identified and have a storage-specific band (analyzed at day 28) not seen in fresh RBCs (analyzed at day 1), as indicated by the white arrow in FIGS. 12A and 12B. The RNA-Seq identified a large number (~40) of transcripts (dark grey dots), besides miR-720 (checkered dot), which increased more than 10 fold induction in the stored RBCs (FIG. 13). In addition, the scatter plots clearly indicate that most of the differences between the stored and fresh RBC are the storage-specific transcripts (FIG. 13). These results support the concept that there are significant changes in the RBC transcriptome during storage. These observations further support the concept that storage-associated transcriptome changes can be used to distinguish stored RBCs from fresh RBCs.

Example 8: Role of Angiogenin in miR-720 Elevation

Figure 14:
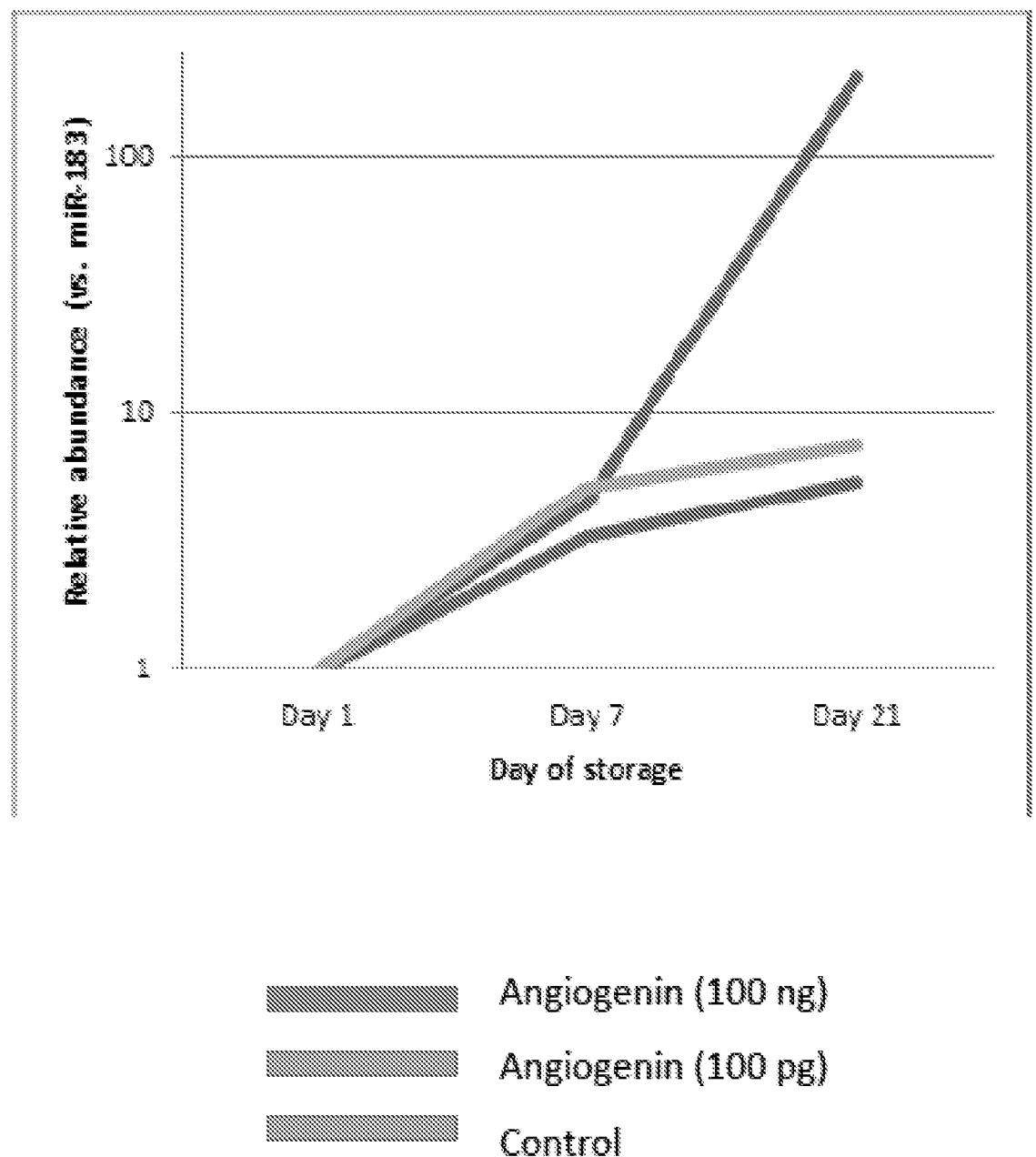
FIG. 14 is a graph showing miR-720 amounts are increased further during storage with the addition of angiogenin.

To determine what accounts for the increase in the tRNA fragment and miR-720 during in vitro storage, the role of angiogenin in the miR-720 elevation was evaluated. Angiogenin is a 14.4-kDa human plasma protein with 65% homology to RNase A that retains the key active site residues and three of the four RNase A disulfide bonds. Angiogenin functions as a cytotoxic tRNA-specific RNase that generate a wide variety of tRNA fragments upon cell stresses (Kilberg et al. (2009) *Trends Endocrinol Metab.* 20:436-43, Yamasaki et al. (2009) *J Cell Biol.* 185:35-42, Emara et al. (2010) *J Biol. Chem.* 285:10959-68, Ivanov et al. (2011) *Mol. Cell.* 43:613-23)). First, different levels (100 pg and 100 ng) of recombinant angiogenin were added to the stored red cells. While the miR-720 dramatically increased in the untreated samples (FIG. 14), the added angiogenin led to a dose-dependent further enhancement of the miR-720 induction, up to 100 fold at day 21 (FIG. 14). Since the RT-PCR and qPCR primers are specific for miR-720, these data indicate that the angiogenin had the capacity to enter RBC and affect the processing of a tRNA to generate miR-720 fragments.

Figure 15:
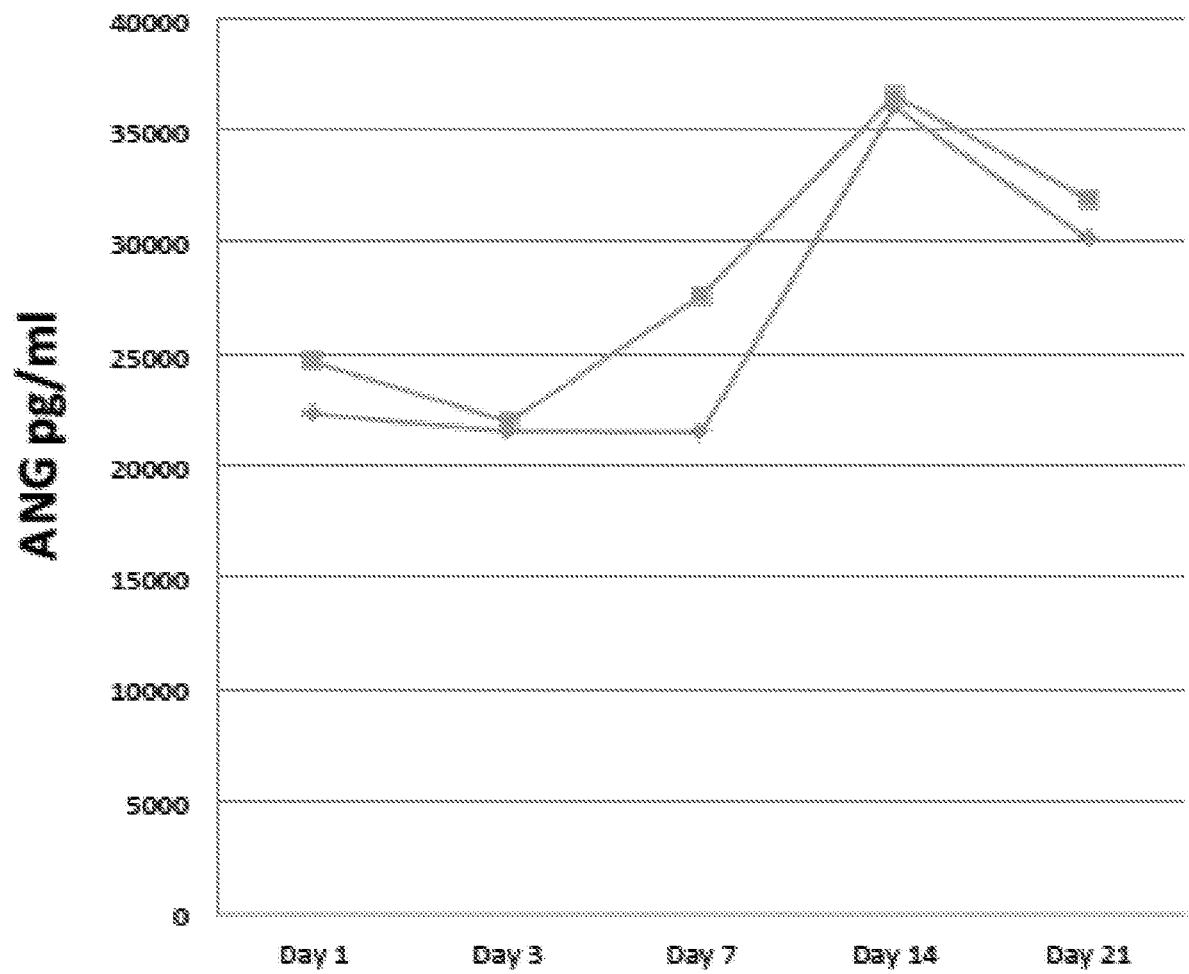
FIG. 15 is a graph showing the increased angiogenin in the supernatants of two stored red cells which have been stored for indicated amount of time.

The level of angiogenin in the supernatant of the red cells which have been stored at different days was also determined (FIG. 15). These data shown the levels of angiogenin in the supernatant is in the range of 30-50 ng/ml, a level found to have strong ability to process tRNA into miR-720 (FIG. 15). These results indicate that the stress-induced RNAase angiogenin is involved in the progressing of the tRNA precursor into miR-720.

Second, a 70-80% increase in the angiogenin that peaks at 14 days was observed, the time points when the miR-720 reach the highest points (FIG. 15). The induction of miR-720 was further assessed by RT-PCR and Northern blots in additional stored red cell samples. Therefore, there is an increase in the soluble angiogenin during the stored red blood cell that likely contributes to the increased miR-720 in the storage-gene signature. While there are different ways that in vitro storage activates angiogenin, the increase in the level of angiogenin in the storage media outside of the red cells explains the increased tRNA fragmentation.

Figure 16:
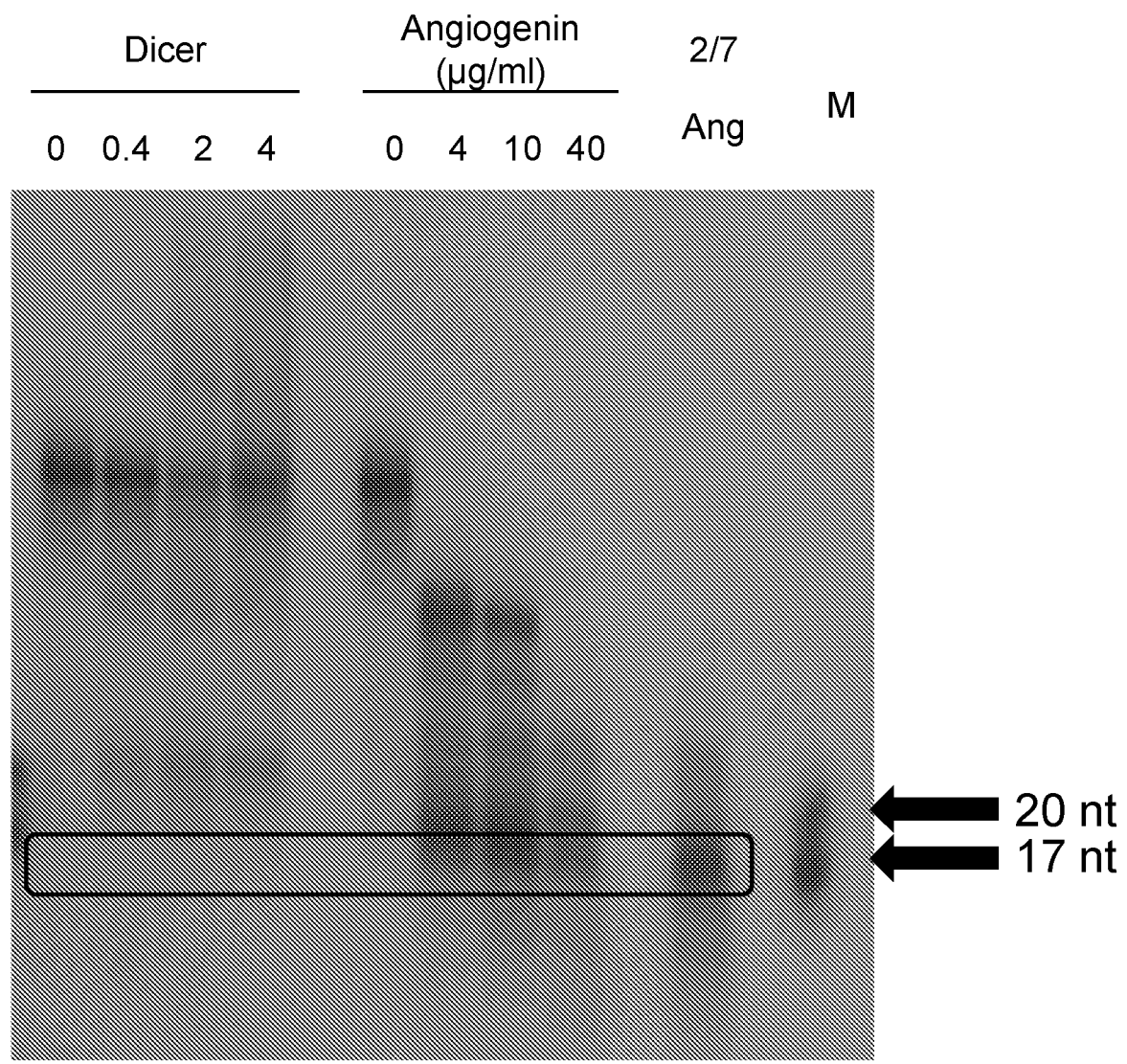
FIG. 16 shows a small RNA northern blot of the miR-720 precursor incubated with indicated levels of recombinant Dicer and angiogenin. The size markers are indicated by arrows and the expected size of mature miR-720 are indicated by the box.

Example 9: Biochemical Assay to Identify the Nucleases Responsible for tRNA Cleavage To identify the nuclease(s) responsible for the tRNA cleavage to generate mature miR-720, the tRNA precursor (called miR-720 precursor) was synthesized for a biochemical assays using small RNA Northern blots. First, the miR-720 precursor was incubated with recombinant Dicer and angiogenin. The products were separated on a PAGE RNA gel, transferred to Nylon membrane and probed with a locked nucleic acid (LNA) probe against mature miR-720. Interestingly, it was found that angiogenin, but not Dicer, potently cleaved miR-720 precursor into a product close to the size of mature miR-720 (FIG. 16).

Example 10: Single Cell Measurement of Storage-Specific Transcripts to Detect ABC An important challenge is that in the real world of blood doping, the transfusion of stored RBCs may only yield a small percentage of transfused RBCs in the circulating blood. For example, the transfusion of one (500 ml) unit of stored blood into a 70 kg individual (~5 liter of circulating blood) yields only a 10% concentration of transfused RBCs in the recipient's peripheral blood. Therefore, any of the storage-specific RNAs will be diluted, which reduces their ability to reliably detect ABT using bulk analysis of whole blood RNAs. Single cell measurement of storage-specific transcripts in individual RBCs will allow detection of ABT in the setting of only a few percent transfused RBCs. Thus, a small population of stored RBCs will be identified by their high expression of storage-specific signatures using flow cytometry, immunofluorescence or other single-cell-based measurements. Once the single cell methods for RNA quantification are optimized, the detection limits of such methods to identify stored RBCs mixed with different amounts of fresh RBCs will be determined.

There will be multiple applications of single cell RNA measurement of storage-specific RNAs to real ABT detection for athletes. A flow cytometry-based assay can be adopted that can evaluate a large number of individual RBCs among various types of blood cells. Additionally, the storage-specific RNAs in individual RBCs can be measured when blood cells are separated on slides, such as through blood smears. To optimize these assays, the single-cell nature, high throughput and well established analytic structures of flow cytometry will be utilized. RNA-fluorescent in situ hybridization (RNA-FISH) technique can be combined with flow cytometry to measure the storage-specific RNA expression within individual cells.

House-keeping genes (miR-183, miR-222) will be used as well as stored-specific transcripts. First, RNA-FISH-Flow cytometry will be performed on the fresh and stored RBC samples and analyze by the flow cytometry to obtain the expression levels of all three RNAs in RBCs. The expression of storage-specific transcripts will be normalized against house-keeping genes to determine whether the stored RBC can be clearly separated from the fresh RBCs. A significantly higher mean fluorescence intensity of the storage-specific signatures will be identified in the stored RBCs compared to the fresh RBCs, but not for the house keeping genes. Once the assays have been optimized on the pure fresh vs. stored RBCs, they will be used to detect the mixed cell populations titrated with different amount of stored RBCs.

Once the single RBC RNA-FISH and flow cytometry for pure "stored" vs. "fresh' RBCs experiments are optimized, their ability to detect stored RBC in a mixed cell population will be determined. For initial studies to validate this methodology in vitro and to determine the lower limit of detection, 500 mL of whole blood will be collected from five donors, process each collection into a CPDA-1 whole blood unit, and store at refrigerated temperatures consistent with standard blood bank practices. At selected times (from 7 to 42 days after collection), donors will return to donate 3 to 5 mL of fresh RBCs. Simultaneously, a 5-mL aliquot will be withdrawn from the stored blood unit obtained from that donor. The donated sample will then be mixed with the fresh sample as an in vitro model of mixing between stored and fresh RBCs that would occur in an athlete doping by ABT. The mixing ratios will be 1% (1 part donated blood to 99 parts fresh blood, representing a 50-mL transfusion into an athlete weighing 70 kg), 4%, 7%, and 10% (10 parts donated blood to 90 parts fresh blood, representing a 500-mL [or 1 blood unit] transfusion to an athlete weighing 70 kg). Each sample will be extracted and tested to determine after each storage interval (7-42 days) and at each transfusion ratio (1-10%) whether doping can be detected by RNA-FISH-flow cytometry analysis of storage-specific transcripts. If necessary these studies may be repeated with a modified protocol to detect blood doping levels as low as 4%. These experiments can determine the detection limit of using storage-specific gene signatures for further optimization for the anti-doping control in the competitive sports.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present invention is well adapted to carry out the objects and obtain the ends and advantages mentioned, as well as those inherent therein. The present disclosure described herein is presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of detecting an autologous blood transfusion or blood doping in a subject suspected of doping, the method comprising:
   isolating a blood sample from the subject;
   measuring the expression level of one or more storage-specific miRNAs-in the subject's red blood cell transcriptome; and
   detecting the presence of stored red blood cells in the sample when the expression level of miR-720 and/or miR-33a-5p is increased and/or the expression level of miR-563 and/or miR-582-5p is decreased when compared to the expression level in a control red blood cell transcriptome.

2. The method of claim 1, wherein the subject's red blood cell transcriptome is generated using one or more red blood cells.

3. The method of claim 1, wherein the expression level of miR-720 and miR-33a-5p is increased when compared to the expression level in the control red blood cell transcriptome.

4. The method of claim 3, wherein miR-720 comprises the nucleic acid sequence set forth in SEQ ID NO:31, and miR-33a-5p comprises the nucleic acid sequence set forth in SEQ ID NO:32.

5. The method of claim 1, wherein the expression level of miR-563 and miR-582-5p is decreased when compared to the expression level in the control red blood cell transcriptome.

6. The method of claim 5, wherein miR-563 comprises the nucleic acid sequence set forth in SEQ ID NO:33 and miR-582-5p comprises the nucleic acid sequence set forth in SEQ ID NO:34.

7. The method of claim 1, further comprising measuring the expression level of at least one RNase in the subject's red blood cell transcriptome, and wherein the expression level of the at least one RNase is increased when compared to that in the control red blood cell transcriptome.

8. The method of claim 7, wherein the at least one RNase comprises a nuclease responsible for tRNA fragmentation.

9. The method of claim 8, wherein the nuclease is angiogenin.

10. The method of claim 1, further comprising generating the subject's red blood cell transcriptome.

11. The method of claim 10, wherein generating the subject's red blood cell transcriptome comprises RNA sequencing.

12. The method of claim 1, further comprising isolating a blood sample from a control subject.

13. The method of claim 12, further comprising generating the control red blood cell transcriptome.

14. The method of claim 13, wherein generating the control red blood cell transcriptome comprises RNA sequencing.

15. The method of claim 1, wherein the subject's red blood cell transcriptome comprises all RNA species.

16. The method of claim 1, wherein the control red blood cell transcriptome comprises all RNA species.

17. The method of claim 12, wherein the control subject comprises a subject not suspected of doping.

18. The method of claim 1, wherein the expression level of miR-720 and miR-33a-5p is increased when compared to the expression level in the control red blood cell transcriptome, and wherein expression level of miR-563 and miR-582-5p is decreased when compared to the expression level in the control red blood cell transcriptome.

19. The method of claim 11, wherein the one or more red blood cells are not lysed prior to RNA sequencing.

20. The method of claim 14, wherein the one or more red blood cells are not lysed prior to RNA sequencing.

* * * * *

SEQUENCE LISTING

<160> NUMBER OF SEQ ID NOS: 34

<210> SEQ ID NO 1
<211> LENGTH: 51
<212> TYPE: DNA
<213> ORGANISM: Homo sapiens

<400> SEQUENCE: 1
gagcagggag caggaagcug ugugugugca gcccugaccu guccuguucu g          51

<210> SEQ ID NO 2
<211> LENGTH: 22
<212> TYPE: DNA
<213> ORGANISM: Homo sapiens

<400> SEQUENCE: 2
tgtagagcag ggagcaggaa gc                                           22

<210> SEQ ID NO 3
<211> LENGTH: 21
<212> TYPE: DNA
<213> ORGANISM: Homo sapiens

<400> SEQUENCE: 3
tgtagagcag ggagcaggaa g                                            21

<210> SEQ ID NO 4
<211> LENGTH: 23
<212> TYPE: DNA
<213> ORGANISM: Homo sapiens

<400> SEQUENCE: 4
tgtagagcag ggagcaggaa gct                                          23

<210> SEQ ID NO 5
<211> LENGTH: 22
<212> TYPE: DNA
<213> ORGANISM: Homo sapiens

<400> SEQUENCE: 5
gccctgacct gtcctgttct gc                                           22

<210> SEQ ID NO 6
<211> LENGTH: 19
<212> TYPE: DNA
<213> ORGANISM: Homo sapiens

-continued

```
<400> SEQUENCE: 6
gccctgacct gtcctgttc                                               19

<210> SEQ ID NO 7
<211> LENGTH: 20
<212> TYPE: DNA
<213> ORGANISM: Homo sapiens

<400> SEQUENCE: 7
gccctgacct gtcctgttct                                              20

<210> SEQ ID NO 8
<211> LENGTH: 21
<212> TYPE: DNA
<213> ORGANISM: Homo sapiens

<400> SEQUENCE: 8
gccctgacct gtcctgttct g                                            21

<210> SEQ ID NO 9
<211> LENGTH: 78
<212> TYPE: DNA
<213> ORGANISM: Homo sapiens

<400> SEQUENCE: 9
cgagggagct gtagagcagg gagcaggaag ctgtgtgtgt ccagccctga cctgtcctgt   60
tctgccccca gcccctca                                                78

<210> SEQ ID NO 10
<211> LENGTH: 21
<212> TYPE: DNA
<213> ORGANISM: Macaca mulatta

<400> SEQUENCE: 10
gccctgacct gttctgttct g                                            21

<210> SEQ ID NO 11
<211> LENGTH: 21
<212> TYPE: DNA
<213> ORGANISM: Microcebus murinus

<400> SEQUENCE: 11
accctgacgt gtcctgctct g                                            21

<210> SEQ ID NO 12
<211> LENGTH: 21
<212> TYPE: DNA
<213> ORGANISM: Rattus rattus

<400> SEQUENCE: 12
gtccatcccc gaccgaccct g                                            21

<210> SEQ ID NO 13
<211> LENGTH: 15
<212> TYPE: DNA
<213> ORGANISM: Mus musculus

<400> SEQUENCE: 13
ccctgactga ccctg                                                   15

<210> SEQ ID NO 14
<211> LENGTH: 15
```

```
<212> TYPE: DNA
<213> ORGANISM: Oryctolagus cuniculus

<400> SEQUENCE: 14
tcctggctct ccctg                                              15

<210> SEQ ID NO 15
<211> LENGTH: 19
<212> TYPE: DNA
<213> ORGANISM: Canis lupus

<400> SEQUENCE: 15
actgacctgt cctgctctg                                          19

<210> SEQ ID NO 16
<211> LENGTH: 17
<212> TYPE: DNA
<213> ORGANISM: Felis catus

<400> SEQUENCE: 16
ctggcctatc ctgctct                                            17

<210> SEQ ID NO 17
<211> LENGTH: 20
<212> TYPE: DNA
<213> ORGANISM: Equus caballus

<400> SEQUENCE: 17
gcgtggcctg tcctgctccg                                         20

<210> SEQ ID NO 18
<211> LENGTH: 19
<212> TYPE: DNA
<213> ORGANISM: Bos taurus

<400> SEQUENCE: 18
ctggccctgt cctgctccg                                          19

<210> SEQ ID NO 19
<211> LENGTH: 21
<212> TYPE: DNA
<213> ORGANISM: Gallus gallus

<400> SEQUENCE: 19
acgatgctct cctctcctct c                                       21

<210> SEQ ID NO 20
<211> LENGTH: 23
<212> TYPE: RNA
<213> ORGANISM: Homo sapiens

<400> SEQUENCE: 20
gcaguauaau uauuuucagg gau                                     23

<210> SEQ ID NO 21
<211> LENGTH: 21
<212> TYPE: RNA
<213> ORGANISM: Homo sapiens

<400> SEQUENCE: 21
gcccugaccu guccuguucu g                                       21

<210> SEQ ID NO 22
```

```
<211> LENGTH: 23
<212> TYPE: RNA
<213> ORGANISM: Homo sapiens

<400> SEQUENCE: 22
gcaguauaau uauuuucacc cau                                              23

<210> SEQ ID NO 23
<211> LENGTH: 23
<212> TYPE: RNA
<213> ORGANISM: Homo sapiens

<400> SEQUENCE: 23
uaauugcuag uguuucagg gau                                               23

<210> SEQ ID NO 24
<211> LENGTH: 21
<212> TYPE: RNA
<213> ORGANISM: Homo sapiens

<400> SEQUENCE: 24
gcccugaccu guccuguucu g                                                21

<210> SEQ ID NO 25
<211> LENGTH: 22
<212> TYPE: RNA
<213> ORGANISM: Homo sapiens

<400> SEQUENCE: 25
uaauugcuag uguuucaccc au                                               22

<210> SEQ ID NO 26
<211> LENGTH: 45
<212> TYPE: RNA
<213> ORGANISM: Homo sapiens

<400> SEQUENCE: 26
uaauaucucg cuggggccuc caaaauguug ugcccagggg uguua                      45

<210> SEQ ID NO 27
<211> LENGTH: 30
<212> TYPE: RNA
<213> ORGANISM: Artificial Sequence
<220> FEATURE:
<223> OTHER INFORMATION: oligonucleotide probe

<400> SEQUENCE: 27
ggcccuauag cucagguua gagcacuggu                                        30

<210> SEQ ID NO 28
<211> LENGTH: 22
<212> TYPE: RNA
<213> ORGANISM: Artificial Sequence
<220> FEATURE:
<223> OTHER INFORMATION: oligonucleotide probe

<400> SEQUENCE: 28
cuuguaaacc aggggucgcg ag                                               22

<210> SEQ ID NO 29
<211> LENGTH: 18
<212> TYPE: RNA
<213> ORGANISM: Artificial Sequence
<220> FEATURE:
<223> OTHER INFORMATION: oligonucleotide probe
```

```
<400> SEQUENCE: 29
aucucgcugg ggccucca                                                        18

<210> SEQ ID NO 30
<211> LENGTH: 75
<212> TYPE: RNA
<213> ORGANISM: Homo sapiens

<400> SEQUENCE: 30
ggcccuauag cucaggguua gagcacuggu cuuguaaacc aggggucgcg aguucaaauc           60
ucgcuggggc cucca                                                           75

<210> SEQ ID NO 31
<211> LENGTH: 17
<212> TYPE: RNA
<213> ORGANISM: Homo sapiens

<400> SEQUENCE: 31
ucucgcuggg gccucca                                                         17

<210> SEQ ID NO 32
<211> LENGTH: 21
<212> TYPE: RNA
<213> ORGANISM: Homo sapiens

<400> SEQUENCE: 32
gugcauugua guugcauugc a                                                    21

<210> SEQ ID NO 33
<211> LENGTH: 19
<212> TYPE: RNA
<213> ORGANISM: Homo sapiens

<400> SEQUENCE: 33
agguugacau acguuuccc                                                       19

<210> SEQ ID NO 34
<211> LENGTH: 23
<212> TYPE: RNA
<213> ORGANISM: Homo sapiens

<400> SEQUENCE: 34
uuacaguugu ucaaccaguu acu                                                  23
```